(12) United States Patent
Macphee et al.

(10) Patent No.: US 11,174,243 B2
(45) Date of Patent: Nov. 16, 2021

(54) SUCCINATE FORMS AND COMPOSITIONS OF BRUTON'S TYROSINE KINASE INHIBITORS

(71) Applicants: Sunesis Pharmaceuticals, Inc., South San Francisco, CA (US); Biogen MA Inc., Cambridge, MA (US)

(72) Inventors: J. Michael Macphee, Cambridge, MA (US); Linda L. Neuman, South San Francisco, CA (US)

(73) Assignees: Sunesis Pharmaceuticals, Inc., South San Francisco, CA (US); Biogen MA Inc., Cambridge, MA (US)

( * ) Notice: Subject to any disclaimer, the term of this patent is extended or adjusted under 35 U.S.C. 154(b) by 0 days.

(21) Appl. No.: 16/319,506

(22) PCT Filed: Jan. 6, 2017

(86) PCT No.: PCT/US2017/012637
§ 371 (c)(1),
(2) Date: Jan. 22, 2019

(87) PCT Pub. No.: WO2018/017153
PCT Pub. Date: Jan. 25, 2018

(65) Prior Publication Data
US 2021/0032218 A1    Feb. 4, 2021

Related U.S. Application Data

(60) Provisional application No. 62/385,202, filed on Sep. 8, 2016, provisional application No. 62/365,353, filed on Jul. 21, 2016.

(51) Int. Cl.
| | | |
|---|---|---|
| *C07D 401/14* | (2006.01) | |
| *A61P 35/00* | (2006.01) | |
| *C07C 55/10* | (2006.01) | |
| *A61K 9/00* | (2006.01) | |

(52) U.S. Cl.
CPC ............ *C07D 401/14* (2013.01); *A61P 35/00* (2018.01); *C07C 55/10* (2013.01); *A61K 9/0053* (2013.01); *C07B 2200/13* (2013.01)

(58) Field of Classification Search
CPC ........ C07D 401/14; C07C 55/10; A61P 35/00
See application file for complete search history.

(56) References Cited

U.S. PATENT DOCUMENTS

| | | | |
|---|---|---|---|
| 4,528,138 A | 7/1985 | Varma et al. | |
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 6,635,762 B1 | 10/2003 | Blumenkopf et al. | |
| 7,300,941 B2 | 11/2007 | Aslanian et al. | |
| 7,312,226 B2 | 12/2007 | Hurley et al. | |
| 7,326,712 B2 | 2/2008 | Hurley et al. | |
| 7,326,713 B2 | 2/2008 | Hurley et al. | |
| 7,335,662 B2 | 2/2008 | Hurley et al. | |
| 7,423,043 B2 | 9/2008 | Rawlins et al. | |
| 7,528,143 B2 | 5/2009 | Noronha et al. | |
| 8,299,077 B2 | 10/2012 | Berthel et al. | |
| 8,362,065 B2 | 1/2013 | Liu et al. | |
| 8,685,880 B2 | 1/2014 | Hommeltoft | |
| 8,785,440 B2 | 7/2014 | Bui et al. | |
| 9,029,359 B2 | 5/2015 | Bui et al. | |
| 9,249,146 B2 | 2/2016 | Bui et al. | |
| 9,266,890 B2 | 2/2016 | Gray et al. | |
| 9,273,028 B2 | 3/2016 | Hopkins et al. | |
| 9,353,087 B2 | 5/2016 | Hopkins et al. | |
| 9,394,277 B2 | 7/2016 | Hopkins et al. | |
| 9,790,229 B2 | 10/2017 | Bui et al. | |
| 9,809,577 B2 | 11/2017 | Hopkins et al. | |
| 9,944,622 B2 | 4/2018 | Hopkins et al. | |
| 2002/0150947 A1 | 10/2002 | Erlanson et al. | |
| 2005/0143372 A1 | 6/2005 | Ghosh et al. | |
| 2006/0189638 A1 | 8/2006 | Rawlins et al. | |
| 2006/0281700 A1 | 12/2006 | Baumann et al. | |
| 2006/0281764 A1 | 12/2006 | Gaul et al. | |
| 2007/0142369 A1 | 6/2007 | van Heek et al. | |
| 2008/0058348 A1 | 3/2008 | Lefrancois et al. | |
| 2008/0108636 A1 | 5/2008 | Honigberg et al. | |
| 2008/0119487 A1 | 5/2008 | Aslanian et al. | |
| 2008/0300242 A1 | 12/2008 | Kuntz et al. | |
| 2010/0093692 A1 | 4/2010 | Aslanian et al. | |
| 2010/0105676 A1 | 4/2010 | Liu et al. | |
| 2010/0160292 A1 | 6/2010 | Whitney et al. | |
| 2012/0004096 A1 | 1/2012 | Hommeltoft | |

(Continued)

FOREIGN PATENT DOCUMENTS

| | | |
|---|---|---|
| CN | 1835943 A | 9/2006 |
| CN | 101610676 A | 12/2009 |

(Continued)

OTHER PUBLICATIONS

Crofford. Expert Review of Clinical Immunology, 2016, 12(7), 763-773 (Year: 2016).*
Vargas. Scandinavian Journal of Immunology, 2013, 130-139 (Year: 2013).*
1125427-13-5, ChemBridge Corporation, Database CAS Registry (Online) [last accessed Mar. 23, 2009], 1 page.
1214417-06-7, ChemBridge Corporation, Database CAS Registry (Online) [last accessed Mar. 25, 2010], 1 page.

(Continued)

*Primary Examiner* — Noble E Jarrell

(74) *Attorney, Agent, or Firm* — Cooley LLP; Heidi A. Erlacher; Christine E. Dunne

(57) ABSTRACT

The present invention provides compounds and compositions thereof which are useful as inhibitors of Bruton's tyrosine kinase and which exhibit desirable characteristics for the same.

19 Claims, 17 Drawing Sheets

(56) References Cited

U.S. PATENT DOCUMENTS

| | | |
|---|---|---|
| 2012/0040961 A1 | 2/2012 | Gray et al. |
| 2012/0058996 A1 | 3/2012 | Liu et al. |
| 2012/0157442 A1 | 6/2012 | Bui et al. |
| 2012/0157443 A1 | 6/2012 | Bui et al. |
| 2013/0345192 A1 | 12/2013 | Hopkins et al. |
| 2014/0308238 A1 | 10/2014 | Rubin-Bejerano et al. |
| 2014/0309212 A1 | 10/2014 | Bui et al. |
| 2015/0126528 A1 | 5/2015 | Hopkins et al. |
| 2015/0158843 A1 | 6/2015 | Hopkins et al. |
| 2016/0304494 A1 | 10/2016 | Hopkins et al. |
| 2016/0311802 A1 | 10/2016 | Hopkins et al. |
| 2016/0318935 A1 | 11/2016 | Hopkins et al. |
| 2016/0376281 A1 | 12/2016 | Bui et al. |
| 2017/0027956 A1 | 2/2017 | Hopkins et al. |
| 2017/0114039 A1 | 4/2017 | Hopkins et al. |
| 2018/0065974 A1 | 3/2018 | Bui et al. |
| 2019/0047986 A1 | 2/2019 | Hopkins et al. |

FOREIGN PATENT DOCUMENTS

| | | |
|---|---|---|
| CN | 101932573 A | 12/2010 |
| CN | 102159214 A | 8/2011 |
| JP | 2008-519059 A | 6/2009 |
| JP | 2010-502751 A | 1/2010 |
| JP | 2012-528103 A | 11/2012 |
| JP | 2013-503905 A | 2/2013 |
| TW | 201120040 A | 6/2011 |
| WO | WO 96/05309 A2 | 2/1996 |
| WO | WO 99/65909 A1 | 12/1999 |
| WO | WO 01/070673 A2 | 9/2001 |
| WO | WO 01/081347 A2 | 11/2001 |
| WO | WO 02/00661 A1 | 1/2002 |
| WO | WO 02/32893 A2 | 4/2002 |
| WO | WO 03/037217 A1 | 5/2003 |
| WO | WO 03/037898 A1 | 5/2003 |
| WO | WO 2004/065380 A1 | 8/2004 |
| WO | WO 2005/117909 A2 | 12/2005 |
| WO | WO 2006/028290 A1 | 3/2006 |
| WO | WO 2006/060461 A1 | 6/2006 |
| WO | WO 2006/071819 A1 | 7/2006 |
| WO | WO 2006/071875 A1 | 7/2006 |
| WO | WO 2006/091450 A1 | 8/2006 |
| WO | WO 2007/011065 A2 | 1/2007 |
| WO | WO 2008/005368 A2 | 1/2008 |
| WO | WO 2008/012635 A2 | 1/2008 |
| WO | WO 2008/014307 A2 | 1/2008 |
| WO | WO 2008/039218 A1 | 4/2008 |
| WO | WO 2008/144253 A1 | 11/2008 |
| WO | WO 2009/098144 A1 | 8/2009 |
| WO | WO 2010/009342 A2 | 1/2010 |
| WO | WO 2010/136423 A1 | 2/2010 |
| WO | WO 2011/029043 A1 | 3/2011 |
| WO | WO 2011/029046 A1 | 3/2011 |
| WO | WO 2012/058645 A1 | 5/2012 |
| WO | WO 2013/185082 A2 | 12/2013 |
| WO | WO 2013/185084 A1 | 12/2013 |
| WO | WO 2016/054627 A1 | 4/2016 |
| WO | WO 2018/017153 A1 | 1/2018 |

OTHER PUBLICATIONS 1214612-86-8, ChemBridge Corporation, Database CAS Registry (Online) [last accessed Mar. 25, 2010], 1 page.

http://www.cancer.gov; "A to Z List of cancers", National Cancer Institute, downloaded May 29, 2014, 22 pages.

Clinical Pharmacology and Biopharmaceutics Reviews, Center for Drug Evaluation and Research, Application No. 205552Orig1s000, submission date: Jun. 28, 2013, Imbruvica, 96 pages; https://www.accessdata.fda.gov/drugsatfda_docs/nda/2013/205552Orig1s000ClinPharmR.pdf).

Imbruvica® (ibrutinib) capsules, for oral use, prescribing information, Revised Jan. 2017, 37 pages.

Advani, R. H. et al., "Bruton Tyrosine Kinase Inhibitor Ibrutinib (PCI-32765) Has Significant Activity in Patients With Relapsed/Refractory B-Cell Malignancies," Journal of Clinical Oncology, 31(1):88-84 (2012).

Alanine, A. et al., "Synthesis and SAR evaluation of 1,2,4-triazoles as A(2A) receptor antagonists," Bioorganic and Medicinal Chemistry Letters, 14(3):817-821 (2004).

Baens, N.P. et al., "Synthesis of 2,5-substituted piperidines: Transposition of 1,4-substitution pattern for the analgesic drug R6582," Tetrahedron, 49(15):3193-3202 (1993).

Banda, N. K. et al., "Complement activation pathways in murine immune complex-induced arthritis and in C3a and C5a generation in vitro," Clin. Exp. Immunol., 159(1):700-708 (2010).

Berge, S. M. et al., "Pharmaceutical salts," Journal of Pharmaceutical Sciences, 66(1):1-19 (1977).

Bhatia, S. K. & Rose, N. R., Ch. 13, "Autoimmunity and Autoimmune Disease," in Principles of Medical Biology, pp. 239-263 (1996).

Binnerts, M. E. et al., "Abstract C186: SNS-062 is a potent noncovalent BTK inhibitor with comparable activity against wild type BTK and BTK with an acquired resistance mutation," Abstracts: AACR-NCI-EORTC International Conference: Molecular Targets and Cancer Tharapeutics; Nov. 5-9, 2015, Boston, MA, 2 pages; doi:10.1158/1535-7163.

Brase, S. et al., "Organic azides: an exploding; diversity of a unique class of compounds," Angewandte Chemie (International Edition in English), 44(33):5188-5240 (2005).

Brinkmann, V. et al., "Fingolimod (FTY720): discovery and development of an oral drug to treat multiple sclerosis," Nature Reviews Drug Discovery, 9:883-897 (2010).

Brown, A. M. & Rampe, D., "Drug-Induced Long QT Syndrome: Is HERG the Root of All Evil," Pharmaceutical News, 7(4):15-20 (2000).

Buggy, J. J. & Elias, L., "Bruton Tyrosine Kinase (BTK) and its Role in B-cell Malignancy," International Reviews of Immunology, (31):119-132 (2012).

Byrd, J. C. et al., "Acalabrutinib (ACP-196) in Relapsed Chronic Lymphocytic Leukemia," N Engl J Med, 374(4):323-332 (2016).

Chabner, B. A. et al., "Chemotherapy of Neoplastic Diseases, Neoplastic Agents," in Goodman & Gilman's The Pharmacological Basis of Therapeutics, L. L. Brunton et al., Eds., 11th Ed., pp. 1315-1403 (2006).

Chan, O. T. M. et al., "The central and multiple roles of B cells in lupus pathogenesis," Immunol. Rev., 169:107-121 (1999).

Chong, P.Y. et al., "Multilevel selectivity in the mild and high-yielding chlorosilane-induced cleavage of carbamates to isocyanates," Journal of Organic Chemistry, 63:8515-8521 (1998).

Cohen, S. B. et al., "Reflex Trial Group. Rituximab for rheumatoid arthritis refractory to anti-tumor necrosis factor therapy: Results of a multicenter, randomized, double-blind, placebo-controlled, phase III trial evaluating primary efficacy and safety at twenty-four weeks," Arthritis Rheum, 54(9):2793-2806 (2006).

Coughlin, C. M. et al., "Approaches and limitations of phosphatidylinositol-3-kinase pathway activation status as a predictive biomarker in the clinical development of targeted therapy," Breast Cancer Res Treat, 124:1-11 (2010).

D'Ambrosio, D. et al., "Chemokine receptors in inflammation: an overview," Journal of Immunological Methods, 273:3-13 (2003).

Denison, T. Y. et al., "Heterogeneity of Cancers and Its Implication for Targeted Drug Delivery," In Cancer Targeted Drug Deliver, An Elusive Dream, Y. H. Bae et al., Eds. (2013), pp. 337-362.

Fabbro, D. et al., "Kinase Inhibitors, Methods and Protocols," in Kinase Inhibitors, Kuster, B., Ed., (2012), 46 pages.

Fine, H. A. et al., Ch. 39, "Neoplasms of the Central Nervous System," in Cancer: Principles & Practice of Oncology, DeVita, V. T. et al., Eds., 7th Ed. (2005), 124 pages.

Flemming, A., "Drug delivery: Nanobioconjugate shrinks brain tumours," Nat. Rev. Drug. Discov., 9(12):917 (2010).

Furze, R. et al., "BLISS-76 Study Group. A Phase III, randomized, placebo-controlled study of belimumab, a monoclonal antibody that inhibits B lymphocyte stimulator, in patients with systemic lupus erythematosus," Arthritis Rheum., 63(12):3918-3930 (2011).

Gao, W. et al., "Selective Antitumor Activity of Ibrutinib in EGFR-Mutant Non-Small Cell Lung Cancer Cells," JNCI J Natl Cancer Inst, 106(9) (2014); dju204 doi:10.1093/jnci/dju204, 4 pages.

(56) References Cited

OTHER PUBLICATIONS

Goldschmidt, T. J. & Holmdahl, R., "Therapeutic effects of monoclonal antibodies to alpha beta TCR but not to CD4 on collagen-induced arthritis in the rat," Cell Immunol, 154(1):240-248 (1994).
Gong, P.K. et al., "Synthesis, monoamine transporter binding, properties, and functional monoamine; uptake activity of 3beta-[4-methylphenyl and 4-chlorophenyl]-2; beta-[5-(substituted phenyl)thiazol-2-yl]tropanes," Journal of Medicinal Chemistry, 50(15):3686-95 (2007).
Hartner, F.W. et al., "Methods for the synthesis of; 5,6,7,8-tetrahydro-1,8-naphthyridine fragments for alphaVbeta3 integrin; antagonists," Journal of Organic Chemistry, 69(25):8723-30 (2004).
Hayter, S. M. & Cook, M. C., "Updated assessment of the prevalence, spectrum and case definition of autoimmune disease," Autoimmunity Reviews, 11:754-765 (2012).
Helfgott, S. M. et al., "Suppressive effects of anti-μ serum on the development of collagen arthritis in rats," Clin. Immunol. Immunopathol., 31(3):403-411 (1984).
Hendriks, R. W. & Kersseboom, R., "Involvement of SLP-65 and Btk in tumor suppression and malignant transformation of pre-B cells," Semin. Immunol., 18(1):67-76 (2006).
Herman, S. E. M. et al., "Bruton tyrosine kinase represents a promising therapeutic target for treatment of chronic lymphocytic leukemia and is effectively targeted by PCI-32765," Blood, 117(23):9287-6296 (2011).
Holmdahl, R. et al., "Chronicity of arthritis induced with homologous type II collagen (CII) in rats is associated with anti-CII B-cell activation," J. Autoimmun., 7(6):739-752 (1994).
Honigberg, L. A. et al., "The Bruton tyrosine kinase inhibitor PCI-32765 blocks B-cell activation and is efficacious in models of autoimmune disease and B-cell malignancy," PNAS, 107(29):13075-13080 (2010).
Huang, J. et al., "The synthesis of 5-substituted ring E analogs of ethyllycaconitine via the Suzuki-Miyaura cross-coupling reaction," Bioorganic and Medicinal Chemistry, 16(7):3816-24 (2008).
Judge, S. I. V. et al., "Potassium channel blockers in multiple sclerosis: Neuronal $K_v$ channels and effects of symptomatic treatment," Pharmacology & Therapeutics, 111:224-259 (2006).
Kagari, T. et al., "Essential role of Fcγ receptors in anti-type II collagen antibody-induced arthritis," J. Immunol., 170(8):4318-4324 (2003).
Kil, L. P. et al., "Bruton's tyrosine kinase mediated signaling enhances leukemogenesis in a mouse model for chronic lymphocytic leukemia," Am J Blood Res, 3(1):71-83 (2013).
Kim, K.-H. et al., "Imidazo[1,5-α]quinoxalines as irreversible BTK inhibitors for the treatment of rheumatoid arthritis," Bioorganic & Medicinal Chemistry Letters, 21:6258-6263 (2011).
Koelink, P. J. et al., "Targeting chemokine receptors in chronic inflammatory diseases: An extensive review," Pharmacology & Therapeutics, 133:1-18 (2012).
Lei, X. et al., "The Akp-Btk value method and the results for the retrieval of the parameters of the Earth's free core nutation," Acta Seismologica Sinica, 13(3):342-350 (2000).
Luo, J. et al., "Principles of cancer therapy: oncogene and non-oncogene addiction," Cell, 136(5):823-837 (2009).
McDermott, U. & Settleman, J., "Personalized Cancer Therapy With Selective Kinase Inhibitors: An Emerging Paradigm in Medical Oncology," 27(33):5650-5659 (2009).
Melgar-Fernandez, R. et al., Synthesis of novel derivatives of (1S,4S)-2,5-Diazabicyclo[2.2.1]heptane and their evaluation as potential ligands in asymmetric catalysis, European Journal of Organic Chemistry, 4:655-672 (2008).
Mehrotra, M.M. et al., "Spirocyclic nonpeptide glycoprotein IIb-IIIa antagonists. Part 3: synthesis and SAR of potent and specific 2,8-diazaspiro[4.5]decanes," Bioorganic and Medicinal Chemistry Letters, 12(7):1103-1107 (2002).
Nakamura, H. et al., "Synthesis of heterocyclic allenes via; palladium-catalyzed hydridetransfer reaction of propargylic amines," Journal of Organic Chemistry, 70(6):2357-2360 (2005).

Navarra, S. V. et al., "BLISS-52 Study Group. Efficacy and safety of belimumab in patients with active systemic lupus erythematosus: a randomised, placebo-controlled, phase 3 trial," Lancet, 377(9767):721-731 (2011).
Pan, Z. et al., Discovery of Selective Irreversible Inhibitors for Bruton's Tyrosine Kinase, ChemMedChem, 2:58-61 (2007).
Panayi, G. S. et al., "Pathogenesis of Rheumatoid Arthritis, The Role of T Cells and Other Beasts," Rheum. Dis. Clin. North Am., 27(2):317-334 (2001).
Penso, M. et al., "A straightforward synthesis of enantiopure 2,6-disubstituted morpholines by a regioselective o-protection/activation protocol," Synlett, 16:2451-2454 (2008).
Pflum, D.A. et al., "Asymmetric synthesis of cetirizine dihydrochloride," Tetrahedron Letters, 43:923-926 (2002).
Phillips, D. P. et al., "Copper-catalyzed C—N coupling of amides and nitrogen-containing heterocycles in the presence of cesium fluoride," Tetrahedron Letters, 50:7293-7296 (2009).
Poupaert, J. H., Drug Design: Basic Principles and Applications, in Encyclopedia of Pharmaceutical Technology, J. Swarbrick, Ed., 3rd Ed., pp. 1362-1369 (2007).
Sainsbury, M., "Heterocyclic Chemistry," E. W. Abel et al., Eds., pp. 97-114 (2001).
Saunders, J. et al., "Novel quinuclidine-based ligands for the muscarinic cholinergic receptor," Journal of Medicinal Chemistry, 33(4):1128-38 (1990).
Sawyers, C. L., "The cancer biomarker problem," Nature, 452:548-552 (2008).
Schousboe, A. et al., "Effects of GABA analogs of restricted conformation on GABA transport in astrocytes and brain cortex slices and on GABA receptor binding," Journal of Neurochemistry, 33(1):181-189 (1979).
Scriven, E. F. V. & Turnbull, K., "Azides: Their preparation and synthetic uses," Chemical Reviews, 88(2):298-368 (1988).
Shafir, A. & Buchwald, S. L., "Highly selective room-temperature copper-catalyzed C—N coupling reactions," Journal of the American Chemical Society, 128(27):8742-3 (2006).
Stuart, J. M. et al., "Type II Collagen-Induced Arthritis in Rats. Passive Transfer with Serum and Evidence That IgG Anticollagen Antibodies Can Cause Arthritis," J. Exp. Med., 155(1):1-16 (1982).
Su, S. et al., "The Structure and Function of Btk family—A Family of Protein Tyrosine Kinases," Journal of Medical Molecular Biology, 3(6):442-445 (2006).
Sutherland, E. R. et al., "Management of Chronic Obstructive Pulmonary Disease," The New England Journal of Medicine, 350:2689-2697 (2004).
Tai, Y.-T. et al., "Bruton tyrosine kinase inhibition is a novel therapeutic strategy targeting tumor in the bone marrow microenvironment in multiple myeloma," Blood, 120(9):1877-1887 (2012).
Uckun, F. et al., "Bruton's tyrosine kinase prevents activation of the anti-apoptotic transcription factor STAT3 and promotes apoptosis in neoplastic B-cells and B-cell precursors exposed to oxidative stress," British Journal of Haematology, 136:574-589 (2007).
Uckun, F. & Qazi, S., "Bruton's tyrosine kinase as a molecular target in treatment of leukemias and lymphomas as well as inflammatory disorders and autoimmunity," Expert Opin. Ther. Patents, 20(11):1457-1470 (2010).
Vassilev, A. O. & Uckun, F. M., "Therapeutic Potential of Inhibiting Bruton's Tyrosine Kinase, (BTK)," Current Pharmaceutical Design, 10:1757-1766 (2004).
Weirich, J. & Antoni, H., "Rate-dependence of antiarrhythmic and proarrhythmic properties of class I and class III antiarrhythmic drugs," Basic Res. Cardiol., 93 Suppl 1:125-132 (1998).
Whyburn, L. R. et al., "Reduced Dosage of Bruton's Tyrosine Kinase Uncouples B Cell Hyperresponsiveness from Autoimmunity in lyn$^{-/-}$ Mice," J Immunol, 171:1850-1858 (2003).
Woyach, J. A. et al., "Bruton's tyrosine kinase (BTK) function is important to the development and expansion of chronic lymphocytic leukemia (CLL)," Blood, 123(8):1207-1213 (2014).
Woyach, J. A. et al., "Resistance Mechanisms for the Bruton's Tyrosine Kinase Inhibitor Ibrutinib," N Engl J Med, 370(24):2286-2294 (2014).

(56) References Cited

OTHER PUBLICATIONS

Wyatt, P.G. et al., "Identification of potent and selective oxytocin antagonists. Part; 1: indole and benzofuran derivatives," Bioorganic and Medicinal Chemistry Letters, 12(10):1399-404 (2002).

Yap, Y. G. & Camm, A. J., "Arrhythmogenic mechanisms of non-sedating antihistamines," Clin. Exp. Allergy, 29 Suppl 3:174-178 (1999).

Zhang, Z. & Bridges, S. L., Jr., "Pathogenesis of Rheumatoid Arthritis, Role of B Lymphocytes," Rheum. Dis. Clin. North Am., 27(2):335-353 (2001).

Zheng W. et al. "Selection of oral bioavailability enhancing formulations during drug discovery", Drug Development and Industrial Pharmacy, vol. 38, Issue 2, 2011, p. 235-247.

STN Registry Database: RN: 1947403-49-7, published on Jul. 7, 2016.

* cited by examiner

| COMPOUND | WT C481 BTK IC$_{50}$ nM | C481S BTK IC$_{50}$ nM | FOLD CHANGE [a] |
|---|---|---|---|
| COMPOUND 1 | 570 | 800 | 1.4 |
| IBRUTINIB | 16 | 1700 | >100 |

[a] EXPRESSED AS IC$_{50}$ OF COMPOUND AGAINST C481S-BTK DIVIDED BY IC$_{50}$ OF COMPOUND AGAINST WT BTK.

Figure 17

SUCCINATE FORMS AND COMPOSITIONS OF BRUTON'S TYROSINE KINASE INHIBITORS

This application is a U.S. National Phase application, filed under 35 U.S.C. § 371, of International Application No. PCT/US2017/012637, filed on Jan. 6, 2017, which claims priority to U.S. provisional patent application No. 62/365,353, filed Jul. 21, 2016, and U.S. provisional patent application No. 62/385,202, filed Sep. 8, 2016, the entire contents of each of which are hereby incorporated by reference.

BACKGROUND OF THE INVENTION

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in hematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk. The present invention fulfills these and other needs.

SUMMARY OF THE INVENTION

It has now been found that novel forms of the present invention, and compositions thereof, are useful as inhibitors of one or more protein kinases and exhibit desirable characteristics for the same. In general, such forms and pharmaceutically acceptable compositions thereof, are useful for treating or lessening the severity of a variety of diseases or disorders as described in detail herein.

BRIEF DESCRIPTION OF THE DRAWINGS

FIG. 17 shows Compound 1 and ibrutinib activity against C481 BTK (WT) and C481S BKT mutant overexpressed in HEK293 cells.

DETAILED DESCRIPTION OF THE INVENTION

Figure 1:
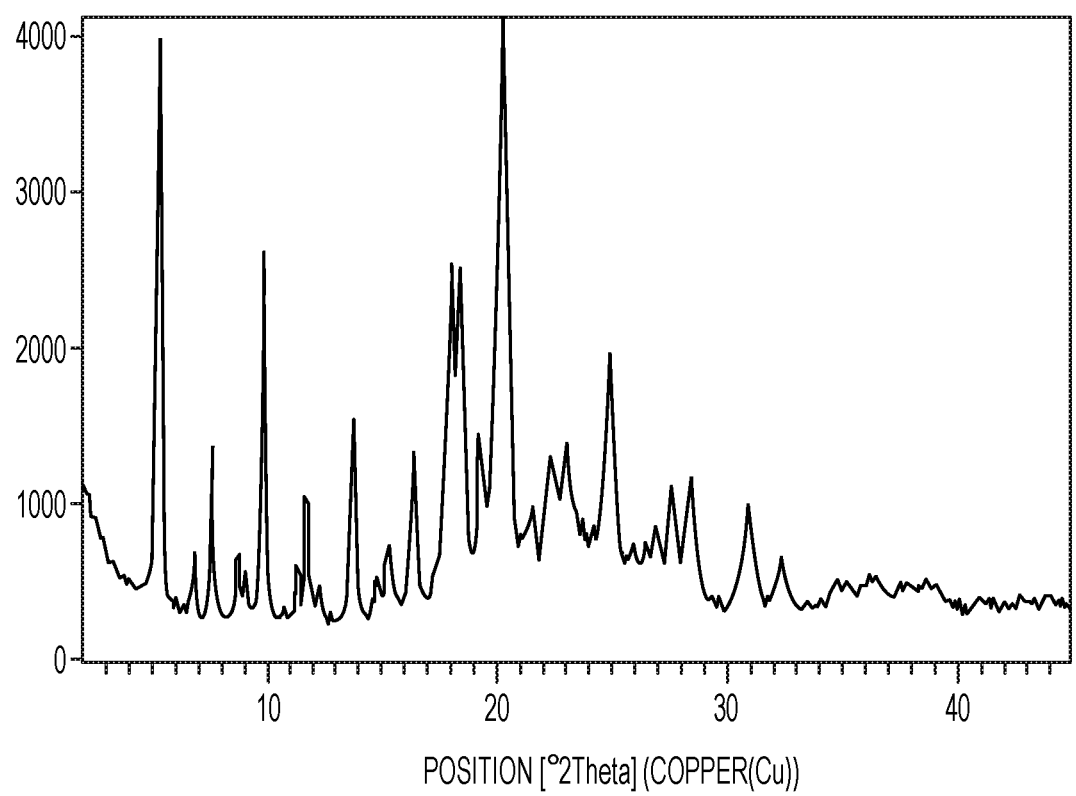
FIG. 1 shows the XRPD pattern for Compound 2 Form 1.

General Description of Certain Aspects of the Invention:

PCT patent publication WO2013/185084 (PCT application PCT/US13/44800, filed Jun. 7, 2013 ("the '800 application")), the entirety of which is hereby incorporated herein by reference, describes certain Btk inhibitor compounds. Such compounds include (3R,3'R,4'S)-1'-(6-amino-5-fluoropyrimidin-4-yl)-3-((3-chloro-5-(trifluoromethyl) phenyl) amino)-2-oxo-[1,3'-bipiperidine]-4'-carboxamide:

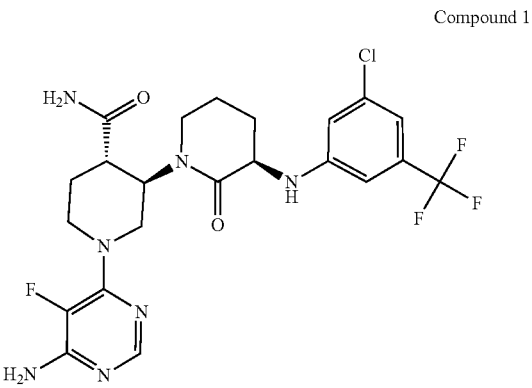 [SMILES: NC(=O)[C@H]1CCN(c2ncnc(N)c2F)C[C@@H]1N1CCC[C@@H](Nc2cc(Cl)cc(C(F)(F)F)c2)C1=O]

Compound 1

Compound 1, which is a freebase, is designated as compound number I-1 in the '800 application. The synthesis of compound 1 is described in detail at Example 2 of the '800 application, which is reproduced herein for ease of reference.

Compound 1 has shown potency against BTK in assays of BTK inhibition (see, e.g., Examples 11-13 of the '800 application). For example, the '800 application reports that Compound 1 has an IC$_{50}$ 0.73 nM as measured in an in vitro Btk kinase assay. Accordingly, compound 1 is useful for treating one or more disorders associated with activity of BTK.

It would be desirable to provide a solid form of compound 1 that imparts characteristics such as improved aqueous solubility, stability, absorption, bioavailability, and ease of formulation and isolation. Accordingly, the present invention provides succinic acid forms of Compound 1 which provide certain such characteristics.

Compound 2 (Succinic Acid×Compound 1)

According to one embodiment, the present invention provides a chemical species Compound 2, comprising Compound 1 and succinic acid.

In some embodiments, Compound 2 is depicted as:

Compound 2

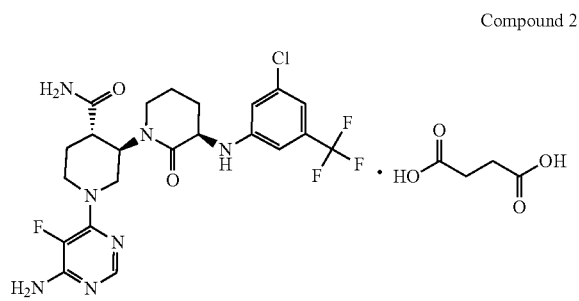 [SMILES: NC(=O)[C@H]1CCN(c2ncnc(N)c2F)C[C@@H]1N1CCC[C@@H](Nc2cc(Cl)cc(C(F)(F)F)c2)C1=O ; O=C(O)CCC(=O)O]

It is contemplated that Compound 2 can exist in a variety of solid forms. When Compound 2 is in solid form, said compound may be amorphous, crystalline, or a mixture thereof. Exemplary solid forms are described in more detail below.

In some embodiments, the present invention provides Compound 2 substantially free of impurities. As used herein, the term "substantially free of impurities" means that the compound contains no significant amount of extraneous matter. Such extraneous matter may include excess succinic acid, excess compound 1, residual solvents, or any other impurities that may result from the preparation of, and/or isolation of, Compound 2. In certain embodiments, at least about 95% by weight of Compound 2 is present. In still other embodiments of the invention, at least about 99% by weight of Compound 2 is present.

According to one embodiment, Compound 2 is present in an amount of at least about 97, 97.5, 98.0, 98.5, 99, 99.5, 99.8 weight percent where the percentages are based on the total weight of the composition. According to another embodiment, Compound 2 contains no more than about 3.0 area percent HPLC of total organic impurities and, in certain embodiments, no more than about 1.5 area percent HPLC total organic impurities relative to the total area of the HPLC chromatogram. In other embodiments, Compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for Compound 2 is also meant to include all tautomeric forms of Compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that Compound 2 can exist in a variety of solid forms. Exemplary such forms include polymorphs such as those described herein.

In some embodiments, Compound 2 is amorphous. In some embodiments, Compound 2 is amorphous, and is substantially free of crystalline Compound 2.

In certain embodiments, Compound 2 is a crystalline solid. In other embodiments, Compound 2 is a crystalline solid substantially free of amorphous Compound 2. As used herein, the term "substantially free of amorphous Compound 2" means that the compound contains no significant amount of amorphous Compound 2. In certain embodiments, at least about 95% by weight of crystalline Compound 2 is present. In still other embodiments of the invention, at least about 99% by weight of crystalline Compound 2 is present.

In some embodiments, Compound 2 has a stoichiometry of (Compound 1):(succinic acid) that is about 1:1.

It has been found that Compound 2 can exist in at least two distinct solid forms.

Compound 2 Form 1

In certain embodiments, the X-ray powder diffraction pattern of Compound 2 Form 1 is substantially similar to the XRPD provided in FIG. 1. In some embodiments, Compound 2 Form 1 has at least 1, 2, 3, 4 or 5 spectral peak(s) selected from the peaks listed in Table A below.

TABLE A

| XRPD Peak Positions for Compound 2 Form 1 Position (±0.2° 2Θ) | |
|---|---|
| 5.33 | 17.91 |
| 6.8 | 18.14 |
| 7.59 | 19.13 |
| 8.71 | 20.12 |
| 9 | 21.42 |
| 9.75 | 22.27 |
| 10.66 | 22.59 |
| 11.26 | 22.9 |
| 11.61 | 24.08 |
| 12.21 | 24.73 |
| 13.69 | 25.72 |
| 14.7 | 26.84 |
| 15.12 | 27.47 |
| 15.2 | 28.3 |
| 16.26 | 30.75 |
| 17.26 | 32.2 |

In some embodiments, Compound 2 Form 1 is characterized in that it has one or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has two or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has three or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has four or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has five or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has six or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has seven or more peaks in its X-ray powder diffraction pattern selected from those at about 5.33, about 7.59, about 9.75, about 13.69, about 17.91, about 18.14, about 20.12, or about 24.73 degrees 2-theta. In some embodiments, Compound 2 Form 1 is characterized in that it has all eight peaks in its X-ray powder diffraction pattern selected from those at about 5.33, about 7.59, about 9.75, about 13.69, about 17.91, about 18.14, about 20.12, or about 24.73 degrees 2-theta. As used herein, the term "about," when used in reference to a degree 2-theta value refers to the stated value±0.2 degree 2-theta.

Methods for preparing Compound 2 Form 1 are described infra.

Compound 2 Form 2

Figure 5:
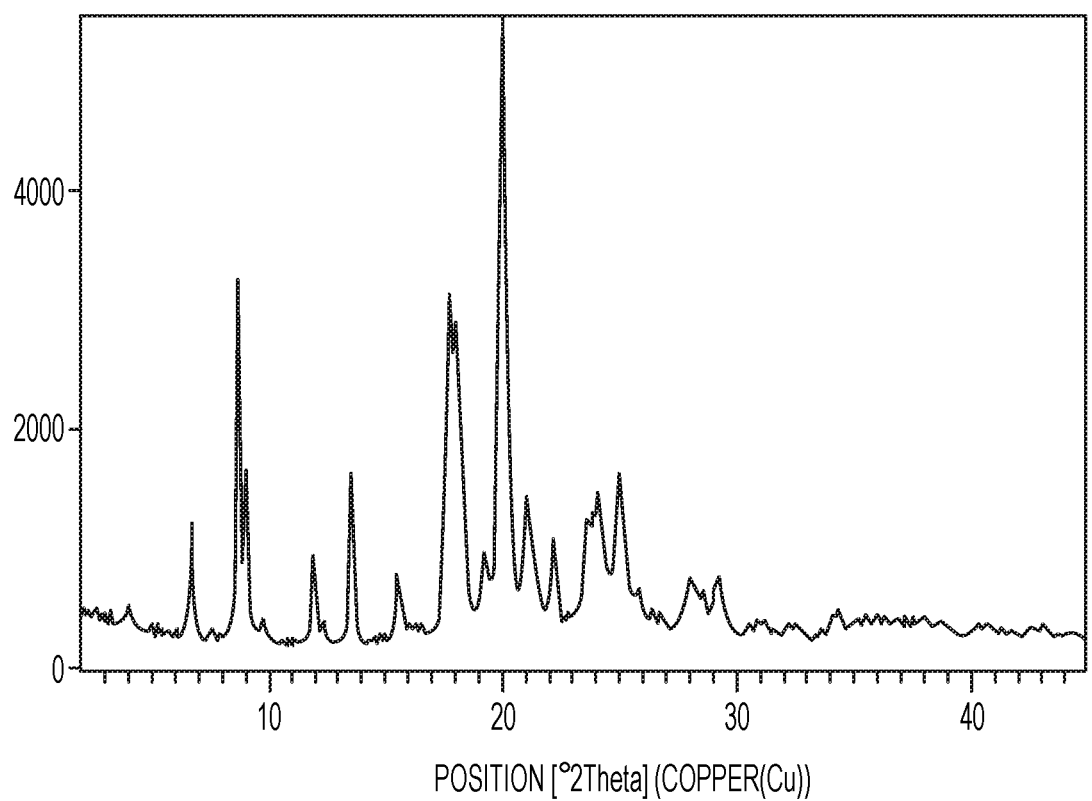
FIG. 5 shows the XRPD pattern for Compound 2 Form 2.
Figure 6:
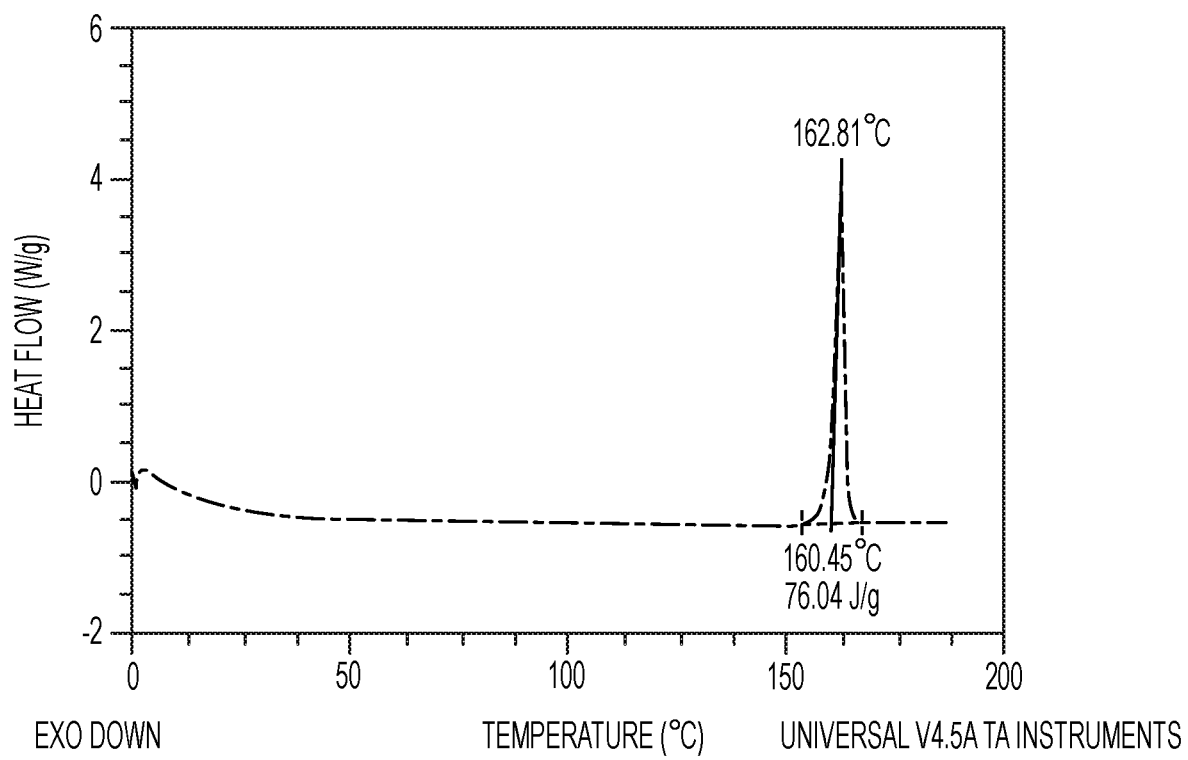
FIG. 6 shows DSC data for Compound 2 Form 2.
Figure 7:
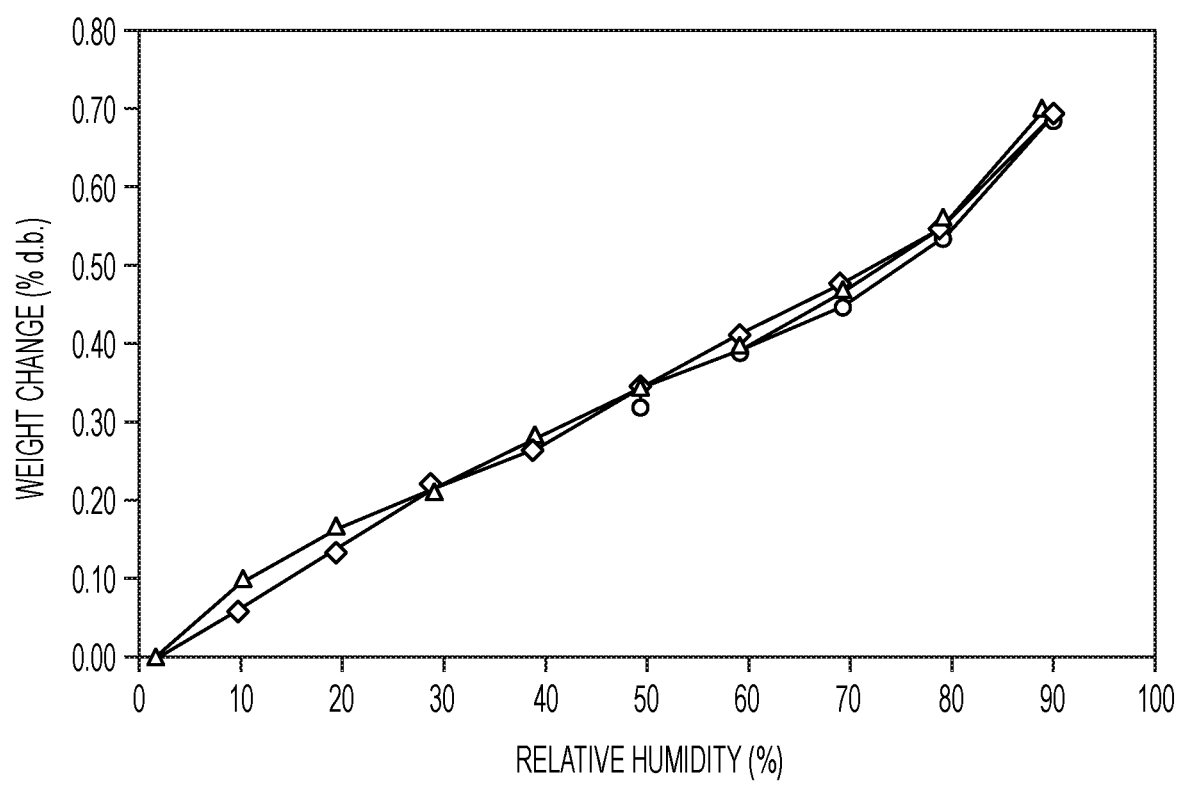
FIG. 7 shows GVS data for Compound 2 Form 2.
Figure 8:
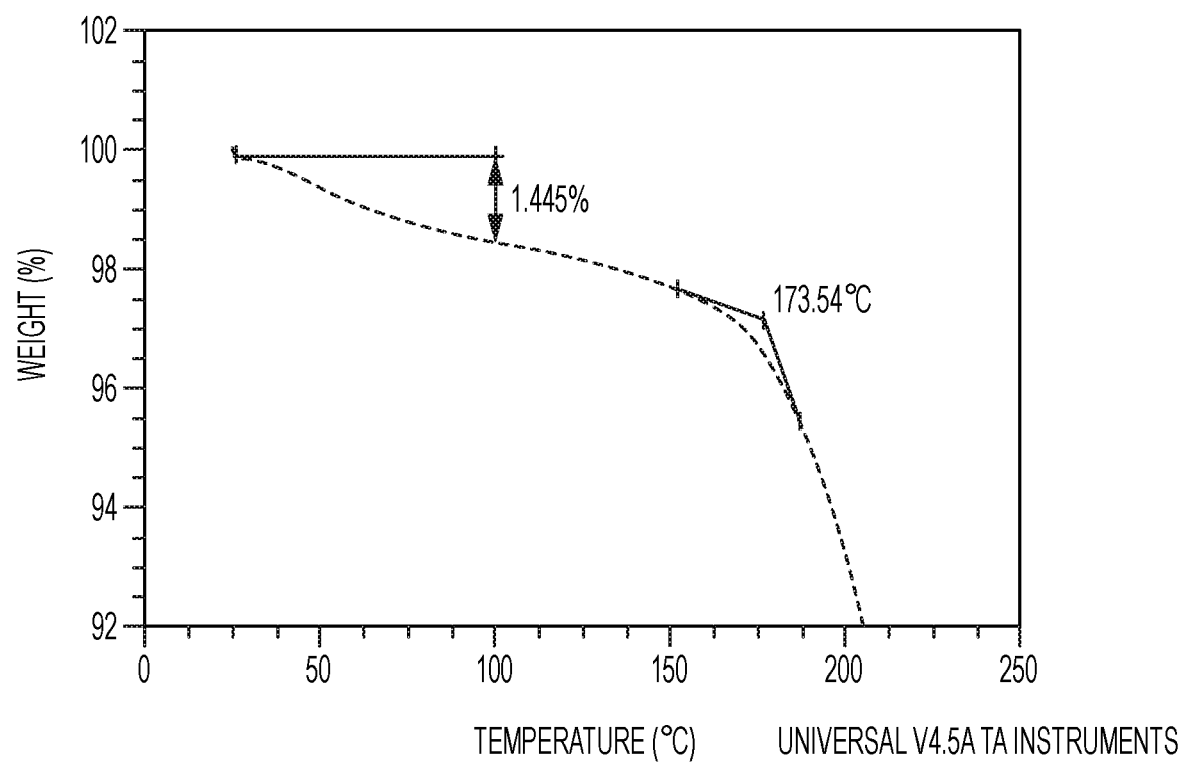
FIG. 8 shows TGA data for Compound 2 Form 2.
Figure 9:
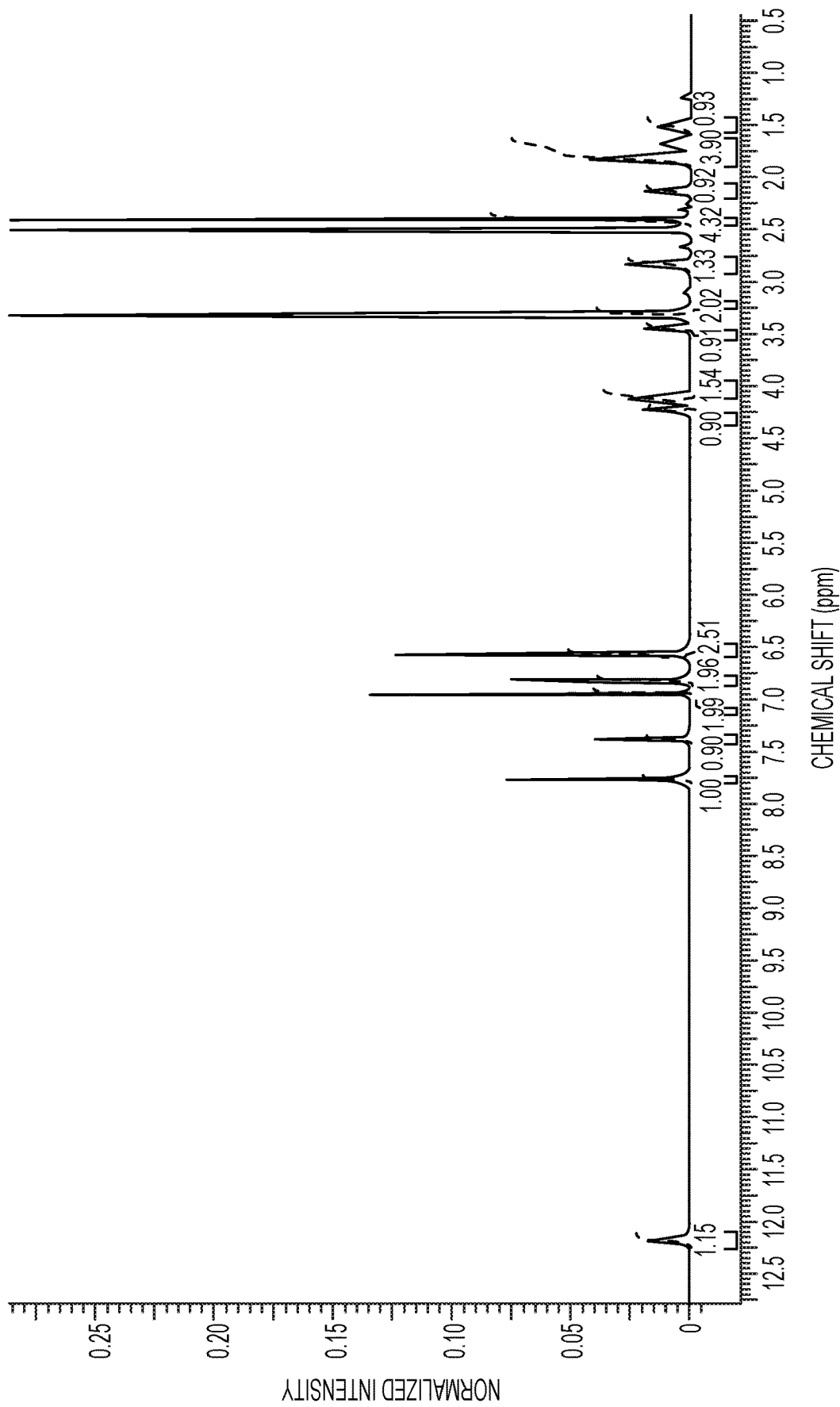
FIG. 9 shows a $^1$H NMR spectrum for Compound 2 Form 2.

In certain embodiments, the X-ray powder diffraction pattern of Compound 2 Form 2 is substantially similar to the XRPD provided in FIG. 5. In some embodiments, Compound 2 Form 2 has at least 1, 2, 3, 4 or 5 spectral peak(s) selected from the peaks listed in Table B below.

TABLE B

| XRPD Peak Positions for Compound 2 Form 2 Position (±0.2° 2Θ) | |
|---|---|
| 4.17 | 22.20 |
| 6.76 | 23.88 |
| 8.77 | 24.46 |
| 9.06 | 25.07 |
| 12.00 | 25.73 |
| 12.43 | 26.51 |
| 13.53 | 28.06 |
| 15.47 | 29.18 |
| 18.13 | 31.17 |
| 19.31 | 32.35 |
| 20.07 | 34.19 |
| 21.28 | |

In some embodiments, Compound 2 Form 2 is characterized in that it has one or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has two or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has three or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has four or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has five or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has six or more peaks in its X-ray powder diffraction pattern selected from those at about 6.76, about 8.77, about 9.06, about 12.00, about 13.53, about 18.13, or about 20.07 degrees 2-theta. In some embodiments, Compound 2 Form 2 is characterized in that it has all seven peaks in its X-ray powder pattern selected from those at about 6.76, about 8.77, about 9.06, about 12.00, about 13.53, about 18.13, or about 20.07 degrees 2-theta.

Methods for preparing Compound 2 Form 2 are described infra.

General Methods of Providing the Compounds

Compound 1 is prepared according to the methods described in detail in the '800 application.

As described herein, Compound 2 and forms thereof, are prepared from Compound 1 by combining Compound 1 with succinic acid to form the product Compound 2. The stoichiometry of Compound 1 and succinic acid can be varied. Thus, another aspect of the present invention provides a method for preparing Compound 2, and forms thereof.

As described generally above, in some embodiments, the present invention provides a method for preparing Compound 2:

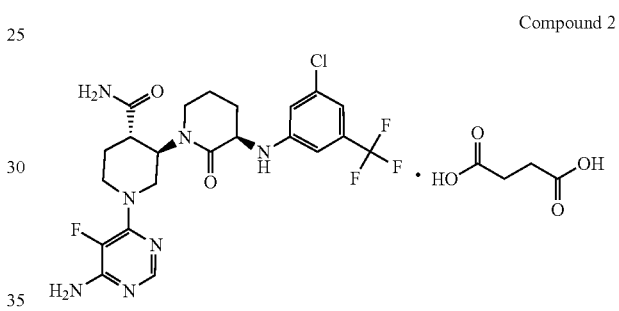

Compound 2 comprising steps of:
combining Compound 1:

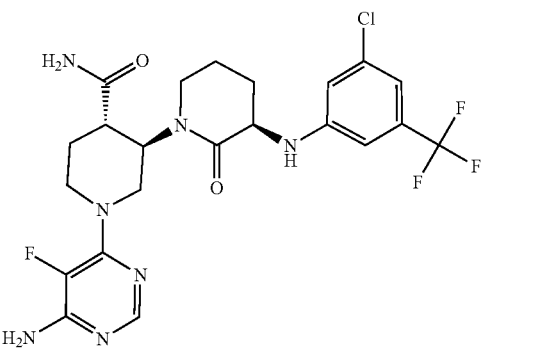

Compound 1 with succinic acid and optionally a suitable solvent under conditions suitable for forming Compound 2.

In some embodiments, the present invention provides a method of making a solid form comprising Compound 1 and succinic acid that is Compound 2 Form 1.

In some embodiments, the present invention provides a method of making a solid form comprising Compound 1 and succinic acid that is Compound 2 Form 2.

In some embodiments, the present invention provides a method of making a solid form comprising Compound 1 and succinic acid that is amorphous.

A suitable solvent may be any solvent system (e.g., one solvent or a mixture of solvents) in which Compound 1 and/or succinic acid are soluble, or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, a solvent is one or more organic alcohols.

In certain embodiments, a suitable solvent is methanol, ethanol, 2-propanol, or acetone wherein said solvent is anhydrous or in combination with water. In some embodiments, suitable solvents include acetone, cyclohexanone, methyl t-butyl ether, 1,4-dioxane, ethyl acetate, isopropyl acetate, methanol, ethanol, 2-propanol, or water. In some embodiments, a suitable solvent is ethanol. In some embodiments, a suitable solvent is anhydrous ethanol. In some embodiments, a suitable solvent is a mixture of ethanol and water. In some embodiments, a suitable solvent is a mixture of ethanol and ethyl acetate.

In some embodiments, the present invention provides a method for preparing Compound 2, comprising steps of removing a solvent and/or adding a solvent. In some embodiments, an added solvent is the same as a solvent removed. In some embodiments, an added solvent is different from a solvent removed. Means of solvent removal are known in the synthetic and chemical arts and include, but are not limited to, any of those described herein and in the ensuing Examples.

In some embodiments, a method for preparing Compound 2 comprises steps of heating and/or cooling a preparation.

In some embodiments, a method for preparing Compound 2 comprises steps of agitating and/or stirring a preparation.

In some embodiments, a method for preparing Compound 2 comprises a step of adding succinic acid to a solution or slurry of compound 1.

In some embodiments, a method for preparing Compound 2 comprises a step of heating.

In certain embodiments, Compound 2 precipitates from the mixture. In some embodiments, Compound 2 crystallizes from the mixture. In some embodiments, Compound 2 crystallizes from solution following seeding of the solution (i.e., adding crystals of Compound 2 to the solution).

Compound 2 can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, Compound 2 is optionally isolated. It will be appreciated that Compound 2 may be isolated by any suitable physical means known to one of ordinary skill in the art. In certain embodiments, precipitated solid Compound 2 is separated from the supernatant by filtration. In other embodiments, precipitated Compound 2 is separated from the supernatant by decanting the supernatant.

In certain embodiments, Compound 2 is separated from the supernatant by filtration.

In certain embodiments, an isolated Compound 2 is dried in air. In other embodiments isolated Compound 2 is dried under reduced pressure, optionally at elevated temperature.

As described herein, Compound 2 can be an amorphous solid. Amorphous solids are well known to one of ordinary skill in the art and can be prepared by various methods such as lyophilization, melting, precipitation (e.g., from super-critical fluid), mechanical treatment (e.g., milling), quench cooling, desolvation, rotary evaporation, precipitation, and spray-drying, among others.

Uses, Formulation and Administration

Among the many types of hematological cancers, B-cell lymphoid malignancies arise from the accumulation of monoclonal, neoplastic B lymphocytes in lymph nodes and often in organs such as blood, bone marrow, spleen, and liver. Variants of these cancers include, for example, non-Hodgkin lymphomas (NHLs)—including chronic lymphocytic leukemia/small lymphocytic lymphoma (CLL/SLL), follicular lymphoma (FL), lymphoplasmacytoid lymphoma/Waldenström's macroglobulinemia (LPL/WM), mantle cell lymphoma (MCL), and diffuse large B-cell lymphoma (DLBCL). These disorders are characterized by lymphadenopathy and splenomegaly and can eventually induce life-threatening organ dysfunction. Patients may also have constitutional symptoms (fevers, night sweats, and/or weight loss) and fatigue. Patients with LPL/WM have an overproduction of immunoglobulin (Ig)M-producing plasma cells and can develop plasma hyperviscosity.

The goal of therapy for these diseases is to induce tumor regression or delay tumor progression in order to control disease-related complications and potentially extend life. Patients who require treatment are commonly given chemotherapeutic and/or immunotherapeutic agents. More and more non-chemotherapy options are available for both front line and relapsed disease, including ibrutinib, venetoclax and idelalisib. Front-line combination therapies can be effective in providing durable remissions, however most patients will eventually experience disease relapse. For any of these cancers, further therapies are given in an attempt to control disease manifestations. Despite use of agents with differing mechanisms of action, progressive resistance to treatment frequently develops. Patients with refractory or multiply relapsed progressive disease (PD) have poor prognoses and are ultimately likely to die of their cancers. Novel mechanisms of action are needed to offer additional treatment options for patients with B-lymphoid malignancies who have experienced disease progression.

Bruton's tyrosine kinase (BTK) is a non-receptor enzyme in the TEC kinase family that is expressed among cells of hematopoietic origin, including B cells, myeloid cells, mast cells, and platelets, where it regulates multiple cellular processes including proliferation, differentiation, apoptosis, and cell migration. BTK activation is implicated in the pathogenesis of several B-cell malignancies (Buggy J J, Elias L. *Int Rev Immunol*. 2012; 31(2):119-32; Herman S E, Gordon A L, Hertlein E, et al. *Blood*. 2011; 117(23):6287-96; Kil L P, de Bruijn M J, van Hulst J A, Langerak A W, Yuvaraj S, Hendriks R W. *Am J Blood Res*. 2013; 3(1):71-83; Tai Y T, Chang B Y, Kong S Y, et al. *Blood*. 2012; 120(9):1877-87; Woyach J A, Bojnik E, Ruppert A S, et al. *Blood*. 2014; 123(8):1207-13).

Ibrutinib (PCI-32765, IMBRUVICA®) is the first therapeutic BTK inhibitor to be approved for use in oncology. This orally delivered, small-molecule, irreversible inhibitor of BTK has been developed for the treatment of B-cell malignancies. In subjects with heavily pretreated FL, MCL, CLL, and LPL/WM, ibrutinib has demonstrated substantial antitumor activity, inducing durable regression of lymphadenopathy and splenomegaly. Based on these studies, ibrutinib has been approved by regulatory authorities in the United States, the European Union (EU), and elsewhere, for the treatment of MCL, CLL, and LPL/WM.

These data support the concept of BTK inhibition as a therapeutic approach to cancer. However, resistance to ibrutinib is observed in the clinic resulting in relapse or loss of disease control, leaving patients with few therapeutic options. Among the mechanisms for tumor progression, an acquired mutation of C481 at the ibrutinib-BTK binding site has been documented as a cause for loss of tumor control in CLL, MCL and WM (Woyach J A, Bojnik E, Ruppert A S, et al. 2014). Patients who develop resistance may also do so through other BTK mutations or mutations downstream of BTK, such as the R665W or L845F mutations in phospholipase C gamma 2 (PLCγ2). The presence of mutations in both BTK and PLCγ2 has also been observed (Woyach, 2014). Moreover, while ibrutinib therapy was not associated with dose-limiting toxicities (DLTs) in the Phase 1 experience the drug can cause adverse events (AEs) with chronic use. These effects may be related to its irreversible off-target inhibition of multiple kinases. Common side effects have included mild-to-moderate diarrhea and rash (IMBRUVICA® US Package Insert, 2016), potentially caused by off-target inhibition of epidermal growth factor receptor (EGFR) (Gao W, Wang M, Wang L, et al. *J Natl Cancer Inst.* 2014; 106(9)). An increased propensity for bruising with occasional serious bleeding has been noted (IMBRUVICA® US Package Insert, 2016), such effects may correlate with TEC kinase involvement in formation of a stable hemostatic plug in response to vascular injury, and data show that simultaneous inhibition of BTK and other TEC kinases by ibrutinib impairs platelet activation. Atrial fibrillation has been seen in 3.5% to 6.5% of trial participants receiving chronic ibrutinib therapy; experimental data implicate the effects of ibrutinib on phosphatidylinositol 3-kinase (PI3K)-AKT activity as the potential cause for this cardiac effect.

The present invention encompasses the recognition that development of a potent inhibitor that, unlike ibrutinib, does not require C481 for interaction with BTK and with unique pharmacokinetics, might circumvent disease resistance in patients with ibrutinib-refractory disease and might offer patients an improved therapeutic profile through an altered selectivity for BTK relative to other kinases.

In certain embodiments, compounds of the present invention are for use in medicine. In some embodiments, the present invention provides method of decreasing enzymatic activity of a kinase in the Tec kinase family (e.g., Tec, Btk, Itk, Txk, Lck, and Bmx). In some embodiments, such methods include contacting a kinase of the Tec kinase family with an effective amount of a Tec kinase family inhibitor. Therefore, the present invention further provides methods of inhibiting Tec kinase family enzymatic activity by contacting a Tec kinase family member with a Tec kinase family inhibitor of the present invention. As used herein, the term "Tec kinase family member" refers to any non-receptor tyrosine kinase in the Tec kinase family. In some embodiments, Tec kinase family members are Tec, Btk, Itk, Txk, Lck, and Bmx.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

The irreversible BTK inhibitors ibrutinib and acalabrutinib have demonstrated effectiveness in various B-cell malignancies (Advani R H, et al. J Clin Oncol. 2013; 31:88-94; Byrd J C, et al. N Engl J Med. 2016; 374:323-32); however, acquired resistance to ibrutinib, due to the Cys481Ser mutation on the kinase active site, has been reported, resulting in substantially reduced activity (Binnerts M E, et al. Mol Cancer Ther. 2015; 14 (12 Suppl 2); Woyach J A, et al. N Engl J Med. 2014; 370:2286-94). Development of C481 resistance mutations is also anticipated in response to acalabrutinib exposure, as reported for a patient who participated in a phase 1/2 clinical trial (Byrd, 2016).

Figure 11:
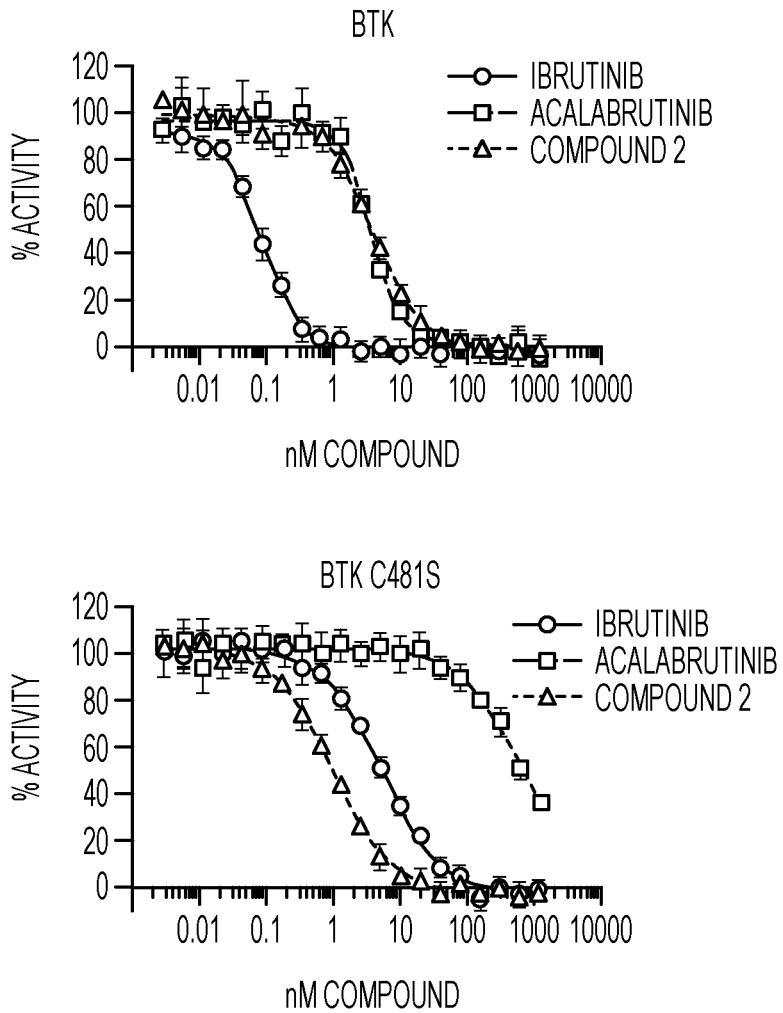
FIG. 11 shows the effects of a Cys481Ser mutation on the activity of covalent BTK inhibitors and the free base of Compound 2.

Compound 1 inhibits BTK activity at subnanomolar concentrations and, unlike covalent BTK inhibitors, does not require interaction with Cys481 on the kinase active site for activity. Compound 1 also has demonstrated inhibition downstream of BTK (e.g., of CD69 expression, phospholipase Cγ [PLCγ] phosphorylation, and FcεR-mediated expression of CD63). The activity of Compound 2 (free base) is unaffected by the Cys481Ser mutation, in contrast to ibrutinib and acalabrutinib. See FIG. 11. The fold change is expressed as $IC_{50}$ of compound against C481S-BTK divided by $IC_{50}$ of compound against WT BTK.

These findings were extended to a cell based assay system using human embryonic kidney 293 (HEK293) cells transfected to overexpress either C481 BTK (wild-type) or C481S BTK (mutant) (see FIG. 17). Compound 1 inhibition of C481 BTK and C481S BTK was similar. However, ibrutinib potency was reduced >100 fold. These data confirm the sensitivity of ibrutinib-mediated BTK inhibition to the C481S mutation and the minimal impact of this mutation on Compound 1 inhibitory activity.

In addition, Compound 1, unlike ibrutinib, does not appreciably inhibit epidermal growth factor receptor (EGFR) and has a restricted kinase selectivity profile (activity toward a panel of 456 kinases and kinase variants was assessed). Compound 1 inhibited 9 kinases, with Km and/or IC50 and/or Kd of <25 nM. In in vitro kinase assays, Compound 1 inhibited BTK, ITK, and TEC with IC50 values of 0.4 nM, 24 nM, and 19 nM, respectively, and demonstrated no significant activity against BMX and TXK (Kd≥200 nM). The kinase selectivity profile of Compound 1 may result in improved safety and tolerability over existing BTK inhibitors due to these differences in selectivity.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration ($IC_{50}$) of the Btk inhibitor against Btk is less than 1 µM. In some embodiments, the $IC_{50}$ of the Btk inhibitor against Btk is less than 500 nM. In some embodiments, the $IC_{50}$ of the Btk inhibitor against Btk is less than 100 nM. In some embodiments, the $IC_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 µM. In some embodiments, the $IC_{50}$ of the Btk inhibitor against Btk is from 0.1 nM to 1 µM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In some embodiments, inhibitors of such Tec kinases are useful for the treatment of diseases and disorders that may be alleviated by inhibiting (i.e., decreasing) enzymatic activity of one or more Tec kinases. The compounds of the invention are effective inhibitors of Tec family kinases and would thus be useful in treating diseases associated with the activity of one or more of the Tec family kinases. The term "diseases" means diseases, syndromes, or disease symptoms. Thus, the present invention provides methods of treating autoimmune disorders, inflammatory disorders, cancers, and precancerous conditions in a subject in need thereof. The present invention further provides methods of treating a disorder responsive to inhibition of Bruton's tyrosine kinase. Such methods include administering to the subject a therapeutically effective amount of an inhibitor of Tec, Btk, Itk, Txk, Lck, and/or Bmx kinase.

In some embodiments, the present invention provides improved methods of treating a patient having a disorder responsive to inhibition of BTK, in which the patient has a BTK Cys481 mutation. In some embodiments, the patient has a functional BTK Cys481 mutation. In some embodiments, a functional BTK Cys481 mutation is selected from C481S, C481F, C481G, or C481T. In some embodiments, a functional BTK Cys481 mutation is C481S. In some embodiments, a patient with such BTK Cys481 mutations has previously received treatment with a BTK inhibitor. In some embodiments, a patient with a BTK Cys481 mutation has previously received treatment with a BTK inhibitor having less activity against BTK with a Cys481 mutation as compared to BTK without a Cys481 mutation. In some embodiments, a patient with a BTK Cys481 mutation has previously received treatment with ibrutinib or acalabrutinib. In some embodiments, the present invention provides methods of treating a patient having a disorder responsive to inhibition of BTK, wherein the BTK is resistant to ibrutinib.

In some embodiments, the present invention provides methods of treating a patient having received one, two, or more prior therapies. In some embodiments, at least one prior therapy was a BTK inhibitor. In some embodiments, a prior therapy BTK inhibitor was ibrutinib or acalabrutinib.

In another aspect, the present invention provides a method of treating a patient having a disorder responsive to inhibition of BTK, in which the patient has been treated with a prior chemotherapeutic and has acquired a mutation that impairs the activity of the prior chemotherapeutic, comprising administering to the patient an effective amount of a provided compound.

WO 2016/054627 A1 discloses a method of treating a hematological cancer in a subject, in which the method comprises a step of monitoring for the presence of an acquired mutation in BTK or PLCγ2, wherein the presence of acquired mutation in BTK or PLCγ2 that affects BTK inhibitor activity is an indication that the subject is becoming resistant to the BTK inhibitor.

In another aspect, the present invention provides a method of treating a patient having a disorder responsive to inhibition of BTK, in which the patient has been treated with a first BTK inhibitor and has acquired a mutation that impairs the activity of the first BTK inhibitor, comprising administering to the patient an effective amount of a provided compound.

In another aspect, the present invention provides a method of treating a patient having a disorder responsive to inhibition of BTK, in which the patient has been treated with a first BTK inhibitor and has acquired a functional BTK Cys481 mutation that impairs the activity of the first BTK inhibitor, comprising administering to the patient an effective amount of a provided compound. As used herein, the term "first BTK inhibitor" includes any known BTK inhibitor, including, by way of nonlimiting example, ibrutinib (PCI-32765), acalabrutinib, BGB-3111, GS-4059, ARQ531, RDX06961, and spebrutinib. In some embodiments, a first BTK inhibitor is a covalent inhibitor of BTK.

In some embodiments, the invention provides a method of treating a subject having a disorder responsive to inhibition of BTK, comprising:
(a) administering to the subject a composition comprising a therapeutically effective amount of a first BTK inhibitor;
(b) obtaining a blood or tissue sample from the subject and extracting DNA therefrom;
(c) analyzing the DNA to identify one or more gene sequences that confer BTK inhibitor resistance to the first BTK inhibitor; and
(d) optionally repeating steps (b) and (c) to monitor for the presence of an acquired mutation that confers BTK inhibitor resistance to the first BTK inhibitor, and
(e) administering to the subject having an acquired mutation that confers BTK inhibitor resistance to the first BTK inhibitor a composition comprising a therapeutically effective amount a provided compound.

In some embodiments, the invention provides a method of treating a subject having a disorder responsive to inhibition of BTK, comprising:
(a) administering to the subject a composition comprising a therapeutically effective amount of a first BTK inhibitor;
(b) obtaining a blood or tissue sample from the subject and extracting DNA therefrom;
(c) analyzing the DNA to identify one or more gene sequences characteristic of BTK, PLCγ2, or a combination thereof; and
(d) optionally repeating steps (b) and (c) to monitor for the presence of an acquired mutation in BTK or PLCγ2 that affects BTK inhibition activity of the first BTK inhibitor, and
(e) administering to the subject having an acquired mutation in BTK or PLCγ2 a composition comprising a therapeutically effective amount a provided compound.

In some embodiments, a disorder responsive to BTK inhibition is a hematological cancer, or other disorder. In some embodiments, the hematological cancer is a B-cell malignancy. In some embodiments, the B-cell malignancy is chronic lymphocytic leukemia, Waldenström's macroglobulinemia, or mantle cell lymphoma.

In some embodiments, the invention provides a method of treating a subject having a disorder responsive to inhibition of BTK, comprising:
(a) obtaining a blood or tissue sample from the subject and extracting DNA therefrom;
(b) analyzing the DNA to identify one or more gene sequences that confer BTK inhibitor resistance; and
(c) administering to the subject having an acquired mutation that confers BTK inhibitor resistance a composition comprising a therapeutically effective amount of a provided compound.

In some embodiments, the invention provides a method of treating a subject having a disorder responsive to inhibition of BTK, comprising:
(a) obtaining a blood or tissue sample from the subject and extracting DNA therefrom;
(b) analyzing the DNA to identify one or more gene sequences characteristic of BTK, PLCγ2, or a combination thereof; to determine the presence of an acquired mutation in BTK or PLCγ2 that affects BTK inhibition activity, and
(c) administering to the subject having an acquired mutation in BTK or PLCγ2 a composition comprising a therapeutically effective amount of a provided compound.

It will be appreciated that, for methods of using provided compounds described herein, the present invention encompasses the use of Compound 1 in such methods.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), hemolytic anemia, autoimmune hepatitis, bullous pemphigoid (BP), Coeliac disease, dermatomyositis, diabetes mellitus type 1, Good Pasture's syndrome, Graves' disease, Guillain-Barré syndrome (GBS), Hashimoto's disease, idiopathic thrombocytopenic purpura, lupus or systemic lupus erythematosus (SLE), mixed connective tissue disease, multiple sclerosis, myasthenia gravis, pemphigus vulgaris, hemophilia with inhibitors, pernicious anemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma (e.g., allergic asthma), atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection (including transplant patients with a positive cross-match) and vasculitis. In certain embodiments, the present invention provides methods of treating disease, disorders, or conditions that approved for treatment with rituximab (a monoclonal antibody against CD20), including non-Hodgkin's lymphoma (NHL), chronic lymphocytic leukemia (CLL), RA, Wegener's granulomatosis (WG), and microscopic polyangiitis (MPA). In some embodiments, the present invention provides a method of treating rheumatoid arthritis (RA), SLE, or atopic dermatitis using compounds disclosed herein.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia (AML), T-cell leukemia, chronic lymphocytic leukemia), multiple myeloma, malignant mesothelioma, malignant melanoma, mantle cell lymphoma, central nervous system lymphoma, diffuse large B-cell lymphoma, and colon cancer (e.g. microsatellite instability-high colorectal cancer). In some embodiments the cancer is characterized by abnormal activity of B-cells, e.g., B-cell malignancies.

In another aspect, the present invention provides methods of treating cancers that are hematologic cancers. In some embodiments, provided methods include administering to the subject a therapeutically effective amount of a provided compound. The term "hematologic cancer" includes bloodborne tumors and diseases or disorders involving abnormal cell growth and/or proliferation in tissues of hematopoietic origin, such as lymphomas, leukemias, and myelomas. Hematologic cancers that may be treated according to the invention include, for example, anaplastic large-cell lymphoma, non-Hodgkin's lymphoma, Hodgkin's lymphoma, B-cell lymphoma (e.g., ABC-diffuse large B-cell lymphoma, GCB-diffuse large B-cell lymphoma), T-cell lymphoma, mantle cell lymphoma (MCL), histiocytic lymphoma, T-cell leukemia, chronic lymphocytic leukemia (CLL), multiple myeloma, chronic myeloid leukemia, acute lymphocytic leukemia, small lymphocytic lymphoma (SLL), lymphoplasmacytoid lymphoma (LPL), acute myelogenous leukemia (AML), acute myeloblastic leukemia, plasma cell leukemia, and Waldenström's macroglobulinemia (WM, also known as lymphoplasmacytic lymphoma).

In some embodiments, the present invention provides a method of treating B lymphoid (B-cell) malignancies.

In some embodiments, the invention provides a method of treating acute myeloid leukemia (such as relapsed or refractory AML) or a myelodysplastic syndrome (MDS).

In some embodiments, the invention provides a method of treating a patient having an autoimmune disorder or cancer or precancerous condition that is resistant to irreversible BTK inhibitors (e.g., ibrutinib, acalabrutinib) due to the acquisition of a Cys481 mutation such as C481S, C481F, C481G, or C481T.

The term "precancerous condition" includes conditions, abnormal tissue growths, and lesions that tend or are likely to become cancerous. Precancerous conditions include, for example, actinic keratosis, adenomatous polyps of the colon, cervical dysplasia, and antecedent hematological disorders such as myelofibrosis, aplastic anemia, paroxysmal nocturnal hemoglobinuria, polycythemia vera, and myelodysplastic syndrome.

In another aspect, the invention provides for the use of a solid form of Compound 2 in the preparation of a medicament for the treatment of a disorder selected from autoimmune disorders, inflammatory disorders, and cancers. In some embodiments, the invention provides a use of the solid form in the preparation of the medicament for the treatment of rheumatoid arthritis, systemic lupus erythematosus, atopic dermatitis, a leukemia, or a lymphoma. In some embodiments, the invention provides a use of the solid form in the preparation of the medicament for the treatment of acute myeloid leukemia or chronic lymphocytic leukemia.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Selected Indications and B Cell Inhibition

As described above, provided compounds are useful for the treatment of disease, including RA and SLE. As described in more detail below, these diseases are affiliated with B cells. Thus, the present disclosure encompasses the recognition that provided compounds are useful as therapeutics for these and other indications. Accordingly, in one aspect the invention provides a method of treating a medical condition, disease, or disorder whose pathology is characterized by abnormal activity of B-cells, comprising administering to a subject an effective amount of a compound of the invention or a composition thereof.

Dysregulation of the immune system is central to the pathogenesis (Panayi G S, et al. *Rheum Dis Clin North Am.* 2001; 27:317-334) of RA. While most of the infiltrating leukocytes in the synovium are T lymphocytes (primarily activated CD4+ T cells) and cells of monocyte/macrophage origin (which release pro-inflammatory cytokines such as IL-1, TNF-alpha and IL-6 and proteolytic enzymes including collagenases and metalloproteinases), B-cells and plasma cells are also found in the synovial fluid (Zhang Z, Bridges S L. *Rheum Dis Clin North Am.* 2001; 27:335-353). A clear role for B cells and their associated effector functions in RA have been demonstrated by the efficacy of rituximab, a selective B cell depleting therapeutic, which is approved for treatment of RA (Cohen S B, et al.; REFLEX Trial Group. *Arthritis Rheum.* 2006 September; 54(9):2793-806).

Although the etiology of SLE is not fully understood, pathogenic autoantibodies and deposition of immune complexes are felt to be critical to the development of widespread tissue damage (Klippel J H, et al. *Primer on the rheumatic diseases.* Atlanta: Arthritis Foundation; 2001).

Autoantibody and immune-complex mediated activation can be studied by measuring inhibition of macrophage activation by macrophages stimulated through Fc receptors (see exemplification—FcγR activation of primary human macrophages). Loss of tolerance to self-antigens ultimately lead to the stimulation of B cells to produce auto-antibodies often directed against nuclear or cytoplasmic components. Antibodies against nuclear components (anti-nuclear antibodies [ANA]) target nuclear antigens including DNA (typically double-stranded DNA [dsDNA]), RNA, histones and small nuclear ribonucleoproteins. These antibodies combine with self-antigens forming immune complexes which deposit in tissues, incite inflammatory reactions and lead to tissue injury. In addition to their roles in pathogenic autoantibody production, B cells also function as antigen-presenting cells (APCs) to T-cells thus playing a role in the initiation of an antigen-specific response. Given the central role of the humoral arm of the immune system in the pathogenesis of SLE, B cells or the B-cell pathway represent desirable therapeutic targets. Belimumab, a monoclonal antibody recently approved for SLE, blocks the binding BAFF to its receptors that are expressed B cells. These receptors serve to activate and potentiate the survival of B cells consistent with a reduction of circulating B cells observed following treatment with belimumab. See also Chan O T, et al. *Immunol Rev.* 1999b; 169:107-121; Navarra S V, et al. Lancet. 2011 Feb. 26; 377(9767):721-31; Furie R, et al. *Arthritis Rheum.* 2011 December; 63(12):3918-30. The role of B cells and myeloid lineage cells in autoimmune diseases such as SLE is further supported by a recent publication which describes efficacy in a preclinical SLE animal model when mice are treated with a small molecule irreversible Btk inhibitor (Honigberg, L A *PNAS.* 2010; 107: 13075).

Combinations

In certain embodiments, a compound of the present invention is administered in combination with another agent. In some embodiments, a compound of the present invention is useful for treating RA and is administered in combination with a disease-modifying antirheumatic drugs (DMARD), including without limitation: methotrexate, abatacept, azathioprine, certolizumab, chloroquine and hydroxychloroquine, cyclosporin, D-penicillamine, adalimumab, etanercept, golimumab, gold salts (including auranofin and sodium aurothiomalate), infliximab, leflunomide, minocycline, rituximab, sulfasalazine, tocilizumab, or combinations thereof. In some embodiments, a compound of the present invention is administered in combination with a NSAID or corticosteroid. In some embodiments, a compound of the present invention is useful for treating SLE and is administered in combination with an agent for the treatment of SLE, including without limitation: corticosteroids, antimalarials, belimumab, mycophenolate mofetil (MMF) or mycophenolate sodium, azathioprine, or combinations thereof. In some embodiments, a compound of the present invention is useful for treating atopic dermatitis and is administered in combination with a topical agent for the treatment of atopic dermatitis, including without limitation: topical steroids, tacrolimus, methotrexate, mometasone furoate (MMF), azathioprine, retinoids, or combinations thereof.

In some embodiments, the invention provides a method of treatment of a cancer through combined use of a compound of the present invention or a composition thereof with at least one additional active agent or composition thereof.

Examples of chemotherapeutic anticancer agents that may be used as second active agents in combination with a provided compound include, but are not limited to, alkylating agents (e.g., mechlorethamine, chlorambucil, cyclophosphamide, melphalan, ifosfamide), antimetabolites (e.g., methotrexate), aurora kinase inhibitors (e.g., ZM447439, hesperidin, VX-680 AZD1152); purine antagonists and pyrimidine antagonists (e.g., 6-mercaptopurine, 5 fluorouracil (5-FU), cytarabine (Ara-C), gemcitabine), spindle poisons (e.g., vinblastine, vincristine, vinorelbine, paclitaxel), podophyllotoxins (e.g., etoposide, irinotecan, topotecan), antibiotics (e.g., doxorubicin, daunorubicin, bleomycin, mitomycin), nitrosoureas (e.g., carmustine, lomustine), inorganic ions (e.g., platinum complexes such as cisplatin, carboplatin), enzymes (e.g., asparaginase), hormones (e.g., tamoxifen, leuprolide, flutamide, and megestrol), topoisomerase II inhibitors or poisons, EGFR (Her1, ErbB-1) inhibitors (e.g., gefitinib), antibodies (e.g., bevacizumab, rituximab), IMIDs (e.g., thalidomide, lenalidomide), various targeted agents (e.g., HDAC inhibitors such as vorinostat), Bcl-2 inhibitors, VEGF inhibitors, proteasome inhibitors (e.g., bortezomib, carfilzomib), cyclin-dependent kinase (cdk) inhibitors (e.g., seliciclib), quinolone derivatives (e.g., vosaroxin), and dexamethasone.

In other embodiments, provided compounds may be used in combination therapy with PDK1 inhibitors, e.g., GSK2334470 (GlaxoSmithKline), BX-795, BX-912, and BX-320 (Berlex); Akt inhibitors, e.g., MK-2206 (Merck); PI3K inhibitors, e.g., GDC-0941 (pictilisib; Genentech), idelalisib (Gilead); BTK inhibitors (e.g., GS-4059 (Gilead)).

In the treatment of hematological and solid tumors, second agents can include inhibitors of PD 1/PD-L1, for example, nivolumab, pembrolizumab, pidilizumab, BMS 936559, and MPDL328OA; CTLA-4 inhibitors, for example, ipilimumab and tremelimumab; and phosphatidylserine inhibitors, for example, bavituximab.

In the treatment of acute myelogenous leukemia, second agents include, for example, cytarabine (ara-C), hypomethylating agents (e.g., azacitidine, decitabine), daunorubicin, and vosaroxin.

In the treatment of chronic lymphocytic leukemia, second agents include, for example, BTK inhibitors (e.g., ibrutinib (PCI-32765), acalarabrutinib, spebrutinib), CD20 antagonists, such as anti-CD20 antibodies (e.g., ofatumumab (Genmab™), obinutuzumab (Gazyva™), rituximab (Rituxan™) ibritumomab tiuxetan (Zevalin™), tositumumab, ocaratuzumab, ocrelizumab (OCREVUS™) veltuzumab), B-cell lymphoma-2 (Bcl-2) protein inhibitors (e.g., venetoclax (Venclexta™)), PI3K inhibitors (e.g., pictilisib, idelalisib (Zydelig™), duvelisib), anti-CD74 antibodies (e.g., milatuzumab), and alkylating agents (e.g., chlorambucil).

In some embodiments, a combination of second agents can be used, such as, for example, a combination of CD20 antagonist and a Bcl-2 inhibitor (e.g., rituximab and venetoclax).

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, microcrystalline cellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In some embodiments, pharmaceutical compositions are provided in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. A unit dosage form can be, for example, a capsule or tablet itself, or it can be the appropriate number of any such compositions in package form. Such unit dosage form may contain, for example, from about 0.01 mg/kg to about 250 mg/kg, and may be given in a single dose or in two or more divided doses. Variations in the dosage will necessarily occur depending upon the species, weight and condition of the patient being treated and the patient's individual response to the medicament.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The present disclosure also provides kits comprising pharmaceutical compositions. In certain embodiments, such kits include Compound 2. The kit optionally includes instructions for prescribing the medication. In certain embodiments, the kit includes multiple doses. In certain embodiments, the kit includes a device for administration. The kit may include sufficient quantities of each component to treat a subject for a week, two weeks, three weeks, four weeks, or multiple months. The kit may include a full cycle of therapy.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., a disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above. In certain embodiments, the administered dose is in the range of about 10 mg to about 1000 mg per day, either once, twice, or more than twice daily.

In some embodiments, the administered dose is about 25 mg to about 300 mg. In some embodiments, the administered dose is about 50 mg to about 300 mg. In some embodiments, the administered dose is greater than 300 mg, for example 400 mg or 500 mg. In some embodiments, the administered dose is about 50 mg to about 300 mg, administered once, twice, or more than twice daily. In some embodiments, the administered dose is about 25 mg to about 300 mg, administered once, twice, or more than twice daily. In some embodiments, the administered dose is about 300 mg to about 500 mg, administered once, twice, or more than twice daily. In some embodiments, the administered dose is about 50 mg, about 100 mg, about 200 mg, or about 300 mg. In some embodiments, the administered dose is about 25 mg, about 50 mg, about 100 mg, about 200 mg, about 300 mg, about 400 mg, or about 500 mg. In some embodiments, the administered dose is about 50 mg, about 100 mg, about 200 mg, or about 300 mg, administered once, twice, or more than twice daily. In some embodiments, the administered dose is about 25 mg, about 50 mg, about 100 mg, about 200 mg, about 300 mg, about 400 mg, or about 500 mg, administered once, twice, or more than twice daily. In some embodiments, the administered dose is based upon the amount of Compound 2. In some embodiments, the administered dose is based upon the amount of Compound 1.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

In order that the invention described herein may be more fully understood, the following examples are set forth. It should be understood that these examples are for illustrative purposes only and are not to be construed as limiting this invention in any manner.

EXAMPLES

The examples below are meant to illustrate certain embodiments of the invention, and not to limit the scope of the invention.

General Experimental

Abbreviations

MeOH Methanol
DMSO Dimethyl sulfoxide
EtOH Ethanol
THF Tetrahydrofuran
EtOAc Ethyl acetate
DSC Differential scanning calorimetry
IC Ion chromatography
NMR Nuclear magnetic resonance
TGA Thermogravimetric analysis
XRPD X-ray powder diffraction Instruments and Methods

A. NMR

The samples for NMR analysis were prepared by complete dissolution of an appropriate amount of material in approximately 0.75 mL of NMR solvent (D2O-d6). $^1$H NMR spectra were recorded at 25° C. using a either a Varian INOVA 400 MHz NMR Spectrometer equipped with a Varian ATB probe. A variable number of scans (16-256) was applied, using standard acquisition parameters. The pre-acquisition delay was set to 10 sec whenever NMR quantification was carried out. Appropriate phasing and baseline corrections were applied in processing the spectra.

B. XRPD

The XRPD spectra were collected in transmission mode on an Panalytical X'pert Pro instrument with X'celerator detector using a standard Aptuit method. The data were evaluated using the HighScore Plus software. The instrumental parameters used are listed below.

| Instrumental parameter | Value |
|---|---|
| 2-theta range | 2-45 |
| Step size [° 2-theta] | 0.0170 |
| Time per step [sec] | 60.7285 sec |
| Wavelength [nm] | 0.154060 (Cu K-Alpha1) |
| Rotation [Yes/No] | Yes |
| Slits divergence/antiscatter. | Incident Mask fixed 10 mm; Divergence slits ½, |
| | Antiscat. slits ½ on incident beam; 1/32 on diffracted |

21
-continued

| Instrumental parameter | Value |
|---|---|
| X-ray Mirror | Inc. Beam Cu W/Si focusing MPD, Acceptance Angle 0.8°, Length 55.3 mm |
| Temperature | Room temperature |
| Humidity values [% RH] | Ambient |
| Fixed Slits | 0.02 rad fixed Soller slits on incident and diffracted beam |
| Monochromator | None |
| Detector type | X'celerator (active length 2.122 2theta degree), scanning mode |
| Sample holder | Transmission sample holder. Use Insert to keep thickness at 1 mm, 5 mm diameter |
| Configuration | Transmission |
| Generator voltage/current | 40 KV/40 mA |

C. TGA and DSC

The TGA analyses were run on a TA Q5000 instrument. The DSC analyses were run on a TA Q2000 MDSC instrument. DSC and TGA method details are listed below:

| Instrumental parameter | Value |
|---|---|
| | TGA |
| Balance purge gas [mL/min] | 10 |
| Sample purge gas [mL/min] | 25 |
| Gas | Nitrogen |
| Temperature-Time-Rate | Typically from room temperature to 250/350° C. at 10° C./min |
| Typical sample amount [mg] | Usually from 2 mg to 20 mg |
| Pan [Pt/Al] | Sealed Al (punched) |
| | DSC |
| Cooling [ON/OFF] | ON |
| Gas | Nitrogen |
| Temperature-Time-Rate | From 0° C. to ~340° C. Ramp at 10° C./min. |
| Typical sample amount [mg] | Usually from 0.5 mg to 2.5 mg |
| Pan | Al |

D. HPLC

HPLC runs were performed using the following:
Column Phenomenex Luna C18 (50×2 mm, 3 µm); column temperature 40° C.
Mobile phase A: 0.05% TFA/water; B: 0.05% TFA/acetonitrile
Gradient 0 min 100% A to 8 min 95% B
Flow 1.0 mL/min
Detector UV DAD@220 nm

E. GVS

The GVS analyses were run on a IGA Sorp instrument by Hiden Analytical. The method parameters are listed below.

| Instrumental parameter | Value |
|---|---|
| Type of analysis | Isotherm |
| Operating temperature [° C.] | 25 |
| Temperature stability [° C./min] | 0.2 |
| Humidity values [% RH] | 50-60-70-80-90-80-70-60-50-40-30-20-10-Dry-10-20-30-40-50-60-70-80-90 |
| Flow rate [mL/min] | 500 |
| Fitting functions | F1 |
| Initial conditions | 25° C., 50% RH, start with adsorption scan |
| End status | End or Keep humidity control |

22
Example 1: Preparation of Compound 1

The synthesis of Compound 1 is described in detail at Example 2 of the '800 application, which is reproduced herein for ease of reference.

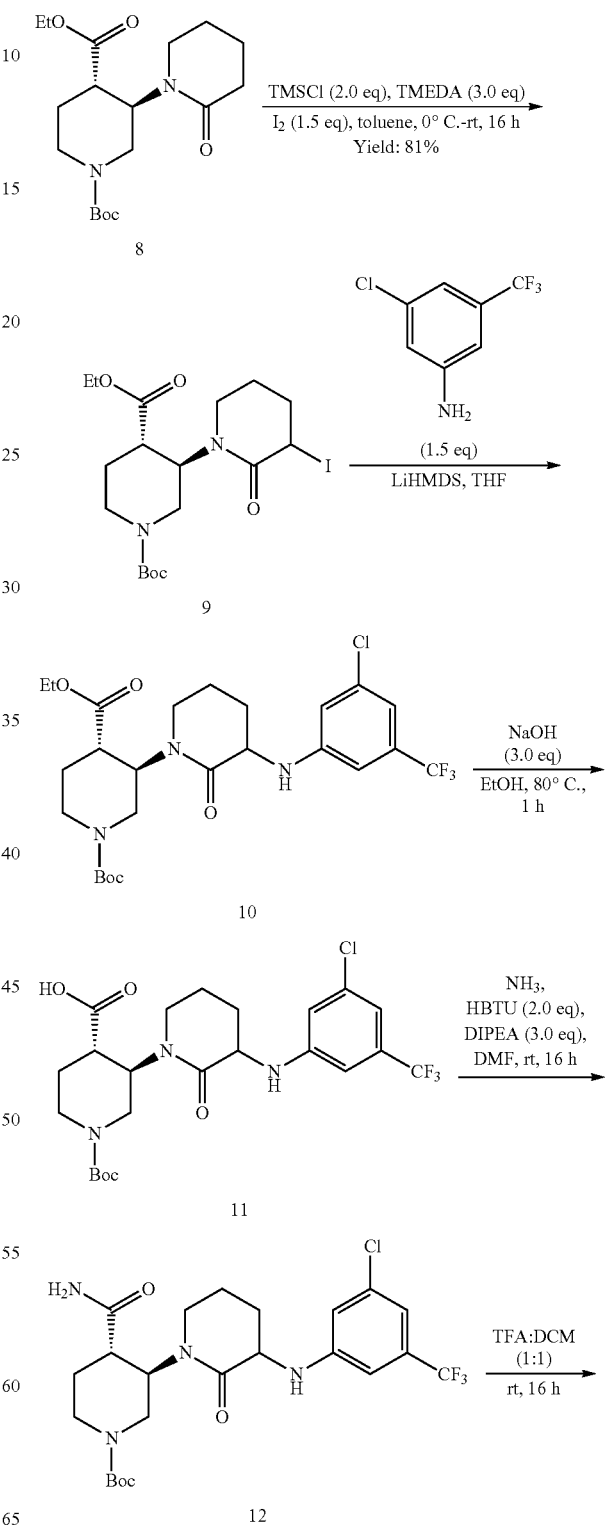

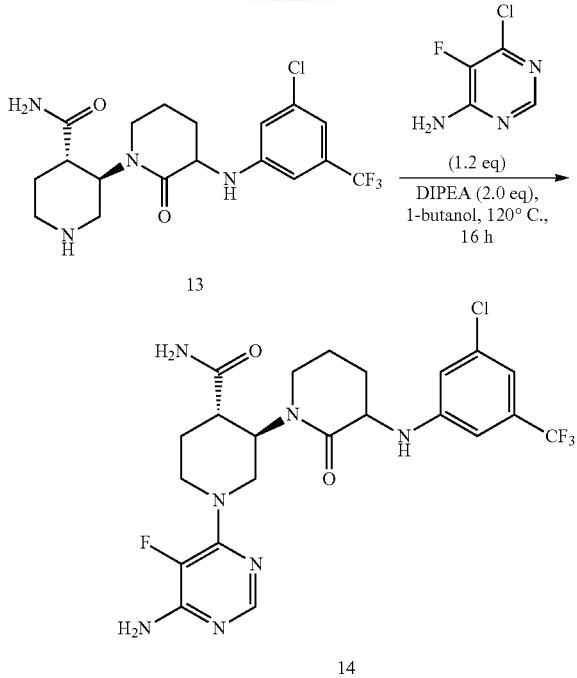

Synthesis of trans-1'-tert-butyl-4'-ethyl-3-iodo-2-oxo-[1,3'-bipiperidine]-1',4'-dicarboxylate. To the solution of trans-1'-tert-butyl 4'-ethyl 2-oxo-[1,3'-bipiperidine]-1',4'-dicarboxylate 8 (141 mg, 2.58 mmol, 1.0 equiv) in dry toluene (10 mL) at 0° C., TMEDA (0.89 g, 7.7 mmol, 3.0 equiv) and TMSCI (0.6 mg, 1.0 mmol, 2.0 equiv) were added successively under $N_2$. After 0.5 h, 12 (0.98 g, 3.87 mmol, 1.5 equiv) was carefully added in small portions. The reaction solution was stirred at 0° C. to rt for 16 h. The mixture was diluted with EtOAc (100 mL), washed with saturated $Na_2S_2O_3$ (20 mL×2) and brine (20 mL), dried ($Na_2SO_4$), filtered, and concentrated in vacuo. The crude product 9 (2.2 g, Y: 81%) was used directly in the next step without further purification. ESI-MS (M+H−56)$^+$: 424.9. $^1$H NMR (400 MHz, CDCl$_3$) δ: 4.78-4.73 (m, 1H), 4.19-4.04 (m, 4H), 3.55-3.30 (m, 4H), 3.24-3.16 (m, 2H), 2.73-2.60 (m, 1H), 2.22-2.14 (m, 2H), 1.96-1.78 (m, 2H), 1.70-1.60 (m, 1H), 1.44 (s, 9H), 1.25 (t, J=7.2 Hz, 3H).

Synthesis of trans-1'-tert-butyl 4'-ethyl 3-((3-chloro-5-(trifluoromethyl) phenyl)amino)-2-oxo-[1,3'-bipiperidine]-1',4'-dicarboxylate. A 1.0 M solution of lithium bis(trimethyldisilyl)amide in THF (13 mL, 12 mmol, 2.0 equiv) was added through an addition funnel at 10-15° C. to a solution of 3-chloro-5-(trifluoromethyl)aniline (15 g, 78 mmol, 1.2 equiv) in THF (13 mL). The mixture was allowed to stir at room temperature for 20 min and a solution of crude trans-1'-tert-butyl-4'-ethyl-3-iodo-2-oxo-[1,3'-bipiperidine]-1',4'-dicarboxylate 9 (3.7 g, 65 mmol, 1.0 equiv) in THF (13 mL) was added through an addition funnel at 10-15° C. over 30 min. After addition, the reaction was allowed to stir at the temperature for 30 min. Upon completion, the reaction was cooled to 5° C. and quenched slowly with water (10 mL), keeping the temperature below 20° C. The quenched reaction was extracted with EtOAc (2×30 mL). The combined organic layers were washed with saturated brine (30 mL), dried ($Na_2SO_4$), filtered, and concentrated in vacuo. The resulting crude product was purified over silica gel eluting with a gradient of 10% to 75% of EtOAc in heptanes to give the desire product 10. ESI-MS (M+H−56)+: 463.1. $^1$H NMR (400 MHz, CDCl$_3$) δ: 6.92 (s, 1H), 6.71-6.69 (m, 2H), 4.17-4.06 (m, 4H), 3.78-3.68 (m, 2H), 3.46-3.36 (m, 3H), 3.23-3.07 (m, 2H), 2.73-2.65 (m, 1H), 2.44-2.37 (m, 1H), 2.03-1.85 (m, 3H), 1.71-1.61 (m, 2H), 1.46 (s, 9H), 1.27-1.19 (m, 3H).

Synthesis of trans-1'-(tert-butoxycarbonyl)-3-((3-chloro-5-(trifluoromethyl) phenyl) amino)-2-oxo-[1,3'-bipiperidine]-4'-carboxylic acid. To a solution of trans-1'-tert-butyl 4'-ethyl 3-((3-chloro-5-(trifluoromethyl)phenyl)amino)-2-oxo-[1,3'-bipiperidine]-1',4'-dicarboxylate 10 (180 mg, 0.33 mmol, 1.0 equiv) in EtOH (5 mL) was added NaOH (40 mg, 0.99 mmol, 3.0 equiv) and solution was stirred at 80° C. for 1 hr. The solvent was concentrated in vacuo and the residue was suspended in water (10 mL) and adjusted to pH=6 with HCl (4 N). The precipitate was filtered to afford (trans)-1'-(tert-butoxycarbonyl)-3-((3-chloro-5-(trifluoromethyl)phenyl)amino)-2-oxo-[1,3'-bipiperidine]-4'-carboxylic acid 11 (150 mg, Y: 82%) as yellow solid which was used next step without further purification. ESI-MS (M+H−85)$^+$: 463.1. $^1$H NMR (400 MHz, CDCl$_3$) δ: 6.85 (s, 1H), 6.82 (s, 1H), 6.78 (s, 1H), 4.12-3.96 (m, 4H), 3.53-3.37 (m, 2H), 3.11-3.04 (m, 2H), 2.75-2.67 (m, 1H), 2.24-2.18 (m, 1H), 1.98-1.89 (m, 3H), 1.71-1.58 (m, 2H), 1.44 (s, 9H).

Synthesis of trans-tert-butyl 4'-carbamoyl-3-((3-chloro-5-(trifluoromethyl) phenyl)amino)-2-oxo-[1,3'-bipiperidine]-1'-carboxylate. To the solution of trans 1'-(tert-butoxycarbonyl)-3-((3-chloro-5-(trifluoromethyl)phenyl)amino)-2-oxo-[1,3'-bipiperidine]-4'-carboxylic acid 11 (70 mg, 0.14 mmol, 1.0 equiv) in DMF (2 mL), was added $NH_4Cl$ (22 mg, 0.41 mmol, 3.0 equiv), HBTU (103 mg, 0.270 mmol, 2.0 equiv) and DIPEA (52 mg, 0.41 mmol, 3.0 equiv). The reaction solution was stirred at rt for 16 h, diluted with EtOAc (10 mL) and washed with water (5 mL) and brine (5 mL). The organic phase was separated and concentrated in vacuo to afford a crude oil which was purified by pre-HPLC (MeOH/H$_2$O with 0.05% TFA as mobile phase) to give the compound (trans)-tert-butyl4'-carbamoyl-3-((3-chloro-5-(trifluoromethyl) phenyl) amino)-2-oxo-[1,3'-bipiperidine]-1'-carboxylate 12 (60 mg, yield: 86%) as a light solid. ESI-MS (M+H−56)$^+$: 463.1. $^1$H NMR (400 MHz, CD$_3$OD) δ: 6.87-6.86 (m, 1H), 6.84-6.83 (m, 1H), 6.80 (s, 1H), 4.11-4.03 (m, 3H), 3.53-3.35 (m, 2H), 3.20-3.08 (m, 2H), 2.77-2.74 (m, 1H), 2.25-2.18 (m, 1H), 1.99-1.88 (m, 3H), 1.70-1.60 (m, 2H), 1.46 (s, 9H).

Synthesis of trans-3-((3-chloro-5-(trifluoromethyl)phenyl)amino)-2-oxo-[1,3'-bipiperidine]-4'-carboxamide. To the solution of trans-tert-butyl 4'-carbamoyl-3-((3-chloro-5-(trifluoromethyl)phenyl)amino)-2-oxo-[1,3'-bipiperidine]-1'-carboxylate 12 (60 mg, 0.11 mmol) in CH$_2$Cl$_2$ (1.0 mL) was added CF$_3$CO$_2$H (1.0 mL) at rt. The reaction mixture was stirred at rt for 2 h, concentrated in vacuo to give desired product 13 (43 mg, 90%) which was used directly in the next step without further purification. ESI-MS (M+H)$^+$: 419.0.

Synthesis of trans-1'-(6-amino-5-fluoropyrimidin-4-yl)-3-((3-chloro-5-(trifluoromethyl)phenyl)amino)-2-oxo-[1,3'-bipiperidine]-4'-carboxamide. To a solution of trans-3-((3-chloro-5-(trifluoromethyl)phenyl)amino)-2-oxo-[1,3'-bipiperidine]-4'-carboxamide 13 (42 mg, 0.10 mmol, 1.0 equiv) in 1-butanol (2 mL), 6-chloro-5-fluoropyrimidin-4-amine (18 mg, 0.12 mmol, 1.2 equiv) was added DIPEA (26 mg, 0.20 mmol, 2.0 equiv). The reaction solution was stirred at 120° C. for 16 h. The mixture was diluted with EtOAc (20 mL), washed with H$_2$O (10 mL) and brine (10 mL), dried (Na$_2$SO$_4$), filtered, and concentrated in vacuo. The crude was by purified by pre-HPLC (MeOH/H$_2$O with 0.05% TFA as mobile phase) to give the compound (trans)-1'-(6-amino- 5-fluoropyrimidin-4-yl)-3-((3-chloro-5-(trifluoromethyl) phenyl)amino)-2-oxo-[1,3'-bipiperidine]-4'-carboxamide 14 (44 mg, yield: 83%) as a yellow solid. ESI-MS (M+H)+: 530.0. HPLC: (214 nm: 100%, 254 nm: 100%). ¹H NMR (400 MHz, CD₃OD) δ: 7.97 (s, 1H), 6.84 (s, 1H), 6.81 (s, 1H), 6.76 (s, 1H), 4.58-4.52 (m, 2H), 4.09-4.03 (m, 1H), 3.52-3.35 (m, 3H), 3.29-3.27 (m, 4H), 3.12-3.05 (m, 1H), 2.24-2.17 (m, 1H), 2.02-1.91 (m, 3H), 1.80-1.63 (m, 2H).

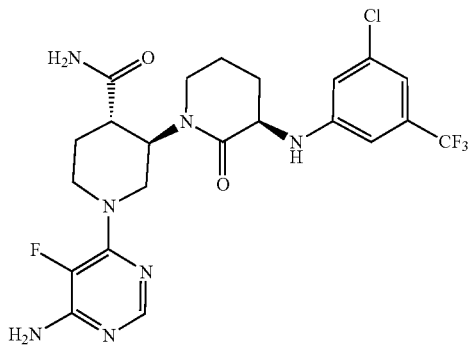 [SMILES: NC(=O)[C@H]1CCN(c2ncnc(N)c2F)C[C@@H]1N1CCC[C@@H](Nc2cc(Cl)cc(C(F)(F)F)c2)C1=O]

(3R,3'R,4'S)-1'-(6-amino-5-fluoropyrimidin-4-yl)-3-((3-chloro-5-(trifluoromethyl) phenyl)amino)-2-oxo-[1,3'-bipiperidine]-4'-carboxamide. The mixture of four diastereomers of compound 14 was separated into three peaks by SFC (IA(2×15 cm), 30% EtOH (0.1% DEA)/CO₂, 100 bar, 60 mL/min) and the title compound corresponded to peak 3. LCMS (Agilent460, 254 nm): ES (+) MS m/e=530.1 (M+1) @ 1.20 min. ¹H NMR (400 MHz, DMSO-d6) δ: 7.77 (d, J=2.01 Hz, 1H), 7.38 (br. s., 1H), 6.94 (s, 2H), 6.75-6.87 (m, 2H), 6.41-6.66 (m, 3H), 4.29 (br. s., 1H), 4.23 (d, J=13.05 Hz, 1H), 3.96-4.18 (m, 2H), 3.44 (td, J=6.15, 12.30 Hz, 1H), 3.24-3.33 (m, 1H), 3.10 (br. s., 1H), 2.88 (br. s., 1H), 2.82 (t, J=12.30 Hz, 1H), 2.13 (qd, J=5.94, 12.30 Hz, 1H), 1.74-1.93 (m, 3H), 1.58-1.74 (m, 1H), 1.41-1.58 (m, 1H).

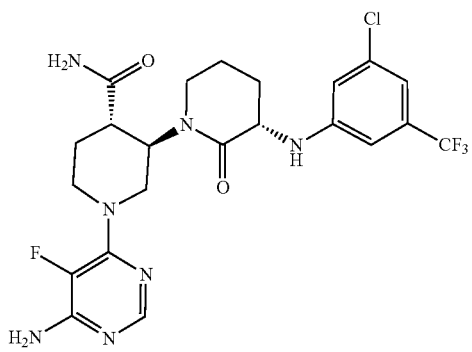 [SMILES: NC(=O)[C@H]1CCN(c2ncnc(N)c2F)C[C@@H]1N1CCC[C@H](Nc2cc(Cl)cc(C(F)(F)F)c2)C1=O]

(3S,3'R,4'S)-1'-(6-amino-5-fluoropyrimidin-4-yl)-3-((3-chloro-5-(trifluoromethyl)phenyl)amino)-2-oxo-[1,3'-bipiperidine]-4'-carboxamide. The mixture of four diastereomers of compound 14 was separated into three peaks by SFC (IA(2×15 cm), 30% EtOH (0.1% DEA)/CO₂, 100 bar, 60 mL/min) and the title compound corresponded to peak 2. LCMS (Agilent460, 254 nm): ES (+) MS m/e=530.1 (M+1) @ 1.19 min. ¹H NMR (400 MHz, DMSO-d6) δ: 7.77 (d, J=1.76 Hz, 1H), 7.39 (br. s., 1H), 6.98 (s, 1H), 6.96 (s, 1H), 6.72-6.88 (m, 2H), 6.57 (s, 2H), 6.54 (d, J=7.78 Hz, 1H), 4.05-4.33 (m, 4H), 3.37 (t, J=6.27 Hz, 2H), 3.11 (br. s., 1H), 2.94 (br. s., 1H), 2.82 (t, J=12.30 Hz, 1H), 2.02-2.16 (m, 1H), 1.75-1.92 (m, 3H), 1.57-1.74 (m, 1H), 1.36-1.54 (m, 1H).

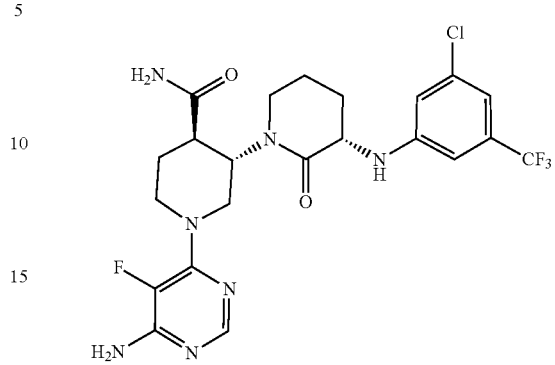

(3S,3'S,4'R)-1'-(6-amino-5-fluoropyrimidin-4-yl)-3-((3-chloro-5-(trifluoromethyl)phenyl)amino)-2-oxo-[1,3'-bipiperidine]-4'-carboxamide. The mixture of four diastereomers of compound 14 was separated into three peaks by SFC (IA(2×15 cm), 30% EtOH (0.1% DEA)/CO₂, 100 bar, 60 mL/min). Peak 1 of 3 was further purified SFC (AD-H (2×15 cm), 30% iPrOH (0.1% DEA)/CO₂, 100 bar, 60 mL/min) to afford the title compound. LCMS (Agilent 460, 254 nm): ES (+) MS m/e=530.1 (M+1) @ 1.20 min. ¹H NMR (400 MHz, DMSO-d6) δ: 7.77 (d, J=1.76 Hz, 1H), 7.38 (br. s., 1H), 6.94 (s, 2H), 6.83 (s, 1H), 6.80 (s, 1H), 6.42-6.66 (m, 3H), 4.18-4.47 (m, 2H), 3.95-4.18 (m, 2H), 3.39-3.52 (m, 1H), 3.24-3.31 (m, 1H), 3.10 (br. s., 1H), 2.88 (br. s., 1H), 2.82 (t, J=12.30 Hz, 1H), 2.13 (qd, J=5.91, 12.39 Hz, 1H), 1.73-1.92 (m, 3H), 1.58-1.73 (m, 1H), 1.42-1.58 (m, 1H).

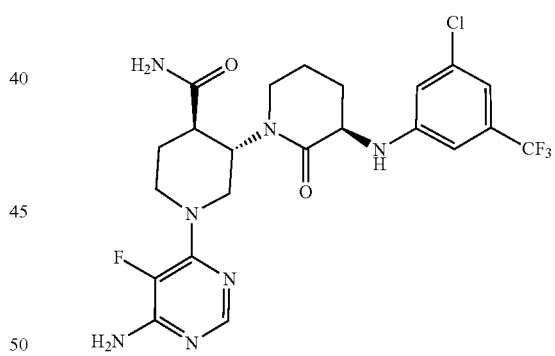

(3R,3'S,4'R)-1'-(6-amino-5-fluoropyrimidin-4-yl)-3-((3-chloro-5-(trifluoromethyl)phenyl)amino)-2-oxo-[1,3'-bipiperidine]-4'-carboxamide. The mixture of four diastereomers of compound 14 was separated into three peaks by SFC (IA(2×15 cm), 30% EtOH (0.1% DEA)/CO₂, 100 bar, 60 mL/min). Peak 1 of 3 was further purified SFC (AD-H (2×15 cm), 30% iPrOH (0.1% DEA)/CO₂, 100 bar, 60 mL/min) to afford the titled compound. LCMS (Agilent 460, 254 nm): ES (+) MS m/e=530.1 (M+1) @ 1.20 min. ¹H NMR (400 MHz, DMSO-d6) δ: 7.77 (d, J=1.76 Hz, 1H), 7.39 (br. s., 1H), 6.98 (s, 1H), 6.96 (s, 1H), 6.73-6.88 (m, 2H), 6.57 (s, 2H), 6.54 (d, J=7.78 Hz, 1H), 4.05-4.35 (m, 4H), 3.37 (t, J=6.15 Hz, 2H), 3.12 (br. s., 1H), 2.94 (br. s., 1H), 2.82 (t, J=12.30 Hz, 1H), 2.09 (sxt, J=5.80 Hz, 1H), 1.74-1.92 (m, 3H), 1.56-1.73 (m, 1H), 1.36-1.52 (m, 1H).

Example 2: Preparation of Compound 2

To 13.4 g of Compound 1, 50 mL of EtOH was added. The resulting slurry was warmed to 60° C. to obtain a clear solution. To this solution, a slurry of succinic acid (4.5 g, 1.5 equiv.) in 50 mL of EtOH was added, and the resulting mixture was heated to reflux to obtain a clear solution. The temperature was decreased to 20-25° C. over 2 hr and stir the mixture at that temperature for 3 hr. The slurry was then filtered and the wet cake was washed with 10 mL cold EtOH (~4° C.). The solid was dried at 50° C. under house vacuum for 12 hr to give 13.0 g of Compound 2 as a white solid (~90% yield) containing 1.4% DMAP (residual from 12% DMAP in starting material).

Example 3: Polymorphs of Compound 2

Polymorph screening was performed on Compound 2 to generate and characterize crystalline forms. A series of solvent systems were selected considering their chemical diversity and compatibility with Compound 2 in order to produce polymorphs. Solvent/water combinations were also used to evaluate the presence of hydrate forms.

Long Term Slurries (LT)

Slurries were set up in the solvents reported in Table 1 by weighing approximately 200 mg of Compound 2, suspending the solid in 0.5 mL of solvent and checking that excess solid remained un-dissolved. The prepared samples were also used to calculate Compound 2 solubility in the solvent systems used.

Compound 2 Solubility

The slurries prepared for the long term slurry experiments were sampled after one day at 20° C. to measure the solubility of Compound 2 in the solvent systems used. The solubility data were obtained by HPLC with respect to a response factor; six samples of Compound 2, dissolved in acetonitrile/methanol 40/60 at known concentration, were prepared and injected in HPLC. The resulting HPLC areas were used to calculate the HPLC response factor for Compound 2 (data not shown). The results of the solubility calculations are reported in Table 1.

TABLE 1

Solubilities of Compound 2 in Various Solvents

| Solvent | Solubility (mg/mL) |
| --- | --- |
| Acetone | 11 |
| Cyclohexanone | 16 |
| Diisopropyl ether | 0 |
| Tert-butylmethyl ether | 1 |
| 1,4-dioxane | 22 |
| Ethyl acetate | 2 |
| Isopropyl acetate | 1 |
| Methanol | 103 |
| Ethanol | 21 |
| 2-propanol | 11 |
| Toluene | 0 |
| Heptane | 0 |
| Water | 1 |
| Methanol/water 90/10 | 100 |
| Ethanol/water 90/10 | 49 |
| 2-propanol/water 90/10 | 41 |

After the solubility calculations, the slurries were stirred at 20° C. for 15 days. The obtained solids were filtered and dried under vacuum at room temperature for ~3 hours prior to XRPD and PLM analyses. Thermal analyses were carried out on certain samples. Table 2 depicts the XRPD results.

The majority of the long term slurries samples showed Form 2 material with an XRPD pattern consistent with the starting material. The ethyl acetate and isopropyl acetate samples showed the conversion of the starting material to Form 1. The water sample showed partial conversion to amorphous material. Ethanol/water 90/10 sample showed a partial conversion of Form 2 to Form 1. DSC data confirmed the presence of these two forms.

TABLE 2

Long Term Slurries physical properties analyses results

| Solvent | Crystal form |
| --- | --- |
| Acetone | Form 2 |
| Cyclohexanone | Form 2 |
| Diisopropyl ether | Form 2 |
| Tert-butylmethyl ether | Form 2 |
| 1,4-dioxane | Form 2 |
| Ethyl acetate | Form 1 |
| Isopropyl acetate | Form 1 |
| Methanol | Form 2 |
| Ethanol | Form 2 |
| 2-propanol | Form 2 |
| Toluene | Form 2 |
| Heptane | Form 2 |
| Water | Amorphous + Form 2 |
| Methanol/water 90/10 | Form 2 |
| Ethanol/water 90/10 | Form 1 + Form 2 |
| 2-propanol/water 90/10 | Form 2 |

Temperature Cycling

Slurries were set up in solvent systems reported above considering the solubility data reported in Table 1. The slurries were stirred for 48 hours switching temperature from 20° C. to 40° C. and vice versa (2 hours at each temperature). Overnight the slurries were stirred at 20° C. The slurries were filtered to isolate the residues; isolated solids were dried under vacuum at room temperature for ~3 hours prior to XRPD and PLM analyses. Thermal analyses were carried out on certain samples. Table 3 depicts the XRPD results. The majority of the temperature cycling samples showed Form 2 material with an XRPD spectrum pattern consistent with the starting material.

The ethyl acetate, isopropyl acetate, and ethanol samples showed partial conversion of the starting material to Form 1. DSC data confirmed the presence of a mixture of Form 1 and Form 2.

The cyclohexanone sample showed an XRPD pattern that could be referred to a mixture of Form 2 and a new crystalline form. DSC data confirmed the presence of Form 2 material and showed an endothermic event at 135° C. that could be related to the new form melting. Cyclohexanone samples analyzed by XRPD after 10 days storing at room temperature showed the tendency to convert to Form 2.

TABLE 3

Temperature cycling physical properties analyses results

| Solvent | Crystal form |
| --- | --- |
| Acetone | Form 2 |
| Cyclohexanone | Form 2 + unknown peaks |
| Diisopropyl ether | Form 2 |
| Tert-butylmethyl ether | Form 2 |
| 1,4-dioxane | Form 2 |
| Ethyl acetate | Form 1 + Form 2 |
| Isopropyl acetate | Form 1 + Form 2 |
| Methanol | Form 2 |
| Ethanol | Form 1 + Form 2 |

TABLE 3-continued

Temperature cycling physical properties analyses results

| Solvent | Crystal form |
|---|---|
| 2-propanol | Form 2 |
| Toluene | Form 2 |
| Heptane | Form 2 |
| Water | Form 2 |
| Methanol/water 90/10 | Form 2 |
| Ethanol/water 90/10 | Form 2 |
| 2-propanol/water 90/10 | Form 2 |

Evaporation

Saturated solutions were set up based on the solubility data reported above. The solutions were filtered through 0.45 mm PTFE filters and the filtrates were allowed to evaporate to dryness in a dry-box at room temperature under nitrogen flux (RH<10%). Solids obtained were analyzed by XRPD and PLM. Thermal analyses were carried out on certain samples. Table 4 depicts the XRPD results. The majority of the evaporation samples showed Form 2 material with an XRPD pattern consistent with the starting material.

The cyclohexanone sample showed an XRPD pattern similar to the temperature cycling cyclohexanone sample. The DSC analysis showed the presence of multiple events that suggested the presence of more than two crystalline forms.

Ethanol and ethanol/water 90/10 samples showed a partial conversion of the starting material to Form 1.

The 1,4-dioxane sample showed a new XRPD pattern. The DSC showed two melting events suggesting the presence of two different forms.

TABLE 4

Evaporation physical properties analyses results

| Solvent | Crystal form |
|---|---|
| Acetone | Form 2 |
| Cyclohexanone | Form 2 + unknown peaks |
| 1,4-dioxane | Unknown form |
| Methanol | Form 2 + unknown peaks |
| Ethanol | Form 1 + Form 2 |
| 2-propanol | Form 2 |
| Methanol/water 90/10 | Form 2 + unknown peaks |
| Ethanol/water 90/10 | Form 1 + Form 2 |
| 2-propanol/water 90/10 | Form 2 |

Sealed Saturated Solutions

Saturated solutions were set up based on the solubility data reported above. The solutions were filtered through 0.45 mm PTFE filters and the filtrates were collected. The filtrates were retained in sealed vials and visually inspected periodically for solid formation at room temperature (15 days). Samples that did not show solid formation were stored firstly at 4° C. (14 days) and then at −20° C. (7 days) if required. Solids obtained were isolated by supernatant removal and dried in a vacuum oven at room temperature prior to analysis by XRPD and PLM. Thermal analyses were carried out on certain samples. Table 5 depicts the XRPD results. Sealed saturated solutions samples showed Form 2 XRPD pattern or mixture of Form 2 with other forms. The cyclohexanone sample showed an XRPD pattern similar to the temperature cycling and evaporation cyclohexanone samples.

TABLE 5

Sealed Saturated Solutions physical properties analyses results

| Solvent | Crystal form |
|---|---|
| Acetone | Form 2 |
| Cyclohexanone | Form 2 + unknown peaks |
| Methanol | Form 2 + unknown peaks |
| Ethanol | Form 1 + Form 2 |
| 2-propanol | Form 2 + unknown peaks |
| Methanol/water 90/10 | Form 2 |
| Ethanol/water 90/10 | Form 2 + unknown peaks |
| 2-propanol/water 90/10 | Form 2 + unknown peaks |

Vapor Diffusion

Figure 10:
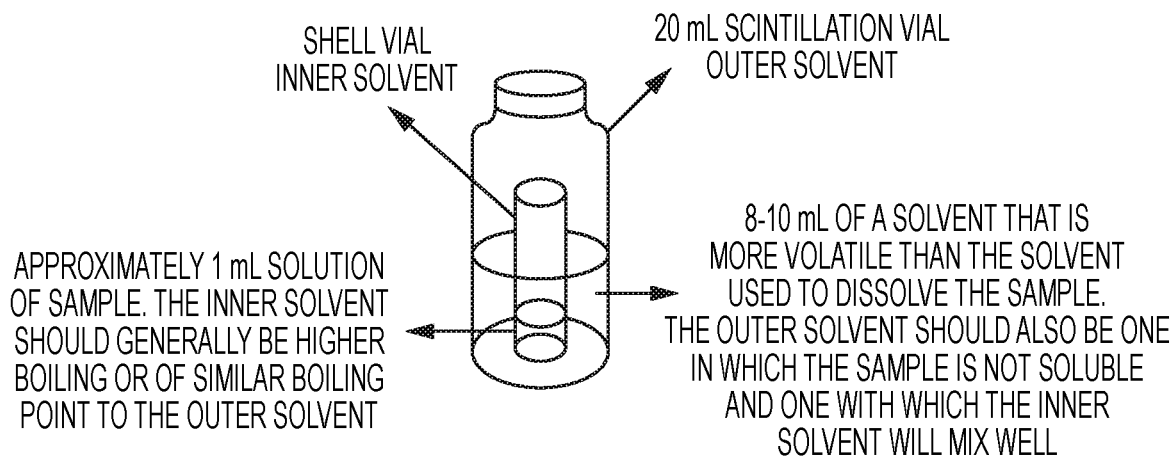
FIG. 10 shows a vapor diffusion experiment set up.

Considering the solubility data reported above, saturated solutions were set up in a range of solvents. The resulting solutions were filtered through 0.45 μm PTFE filters and placed in an environment rich of anti-solvent as depicted in FIG. 10.

Solutions were visually inspected periodically for solid formation. Solids were isolated by removing the supernatants with a pipette and were dried in a vacuum oven at room temperature for ~3 hr prior to analysis by XRPD and PLM. Thermal analyses were carried out on certain samples. Table 6 reports the solvent/antisolvents couples used to set up the experiments and the results.

The samples generated using diisopropyl ether as antisolvent showed an XRPD pattern that appears to be Form 2 material. The presence of some additional XRPD peaks could suggest the presence of another form in the samples. The DSC trace showed a single melting event related to Form 2.

The samples generated using ethyl acetate or isopropyl acetate as antisolvent showed the presence of Form 1 material or mixtures of Form 1 and Form 2.

The solid sample generated by the use of heptane as antisolvent showed the typical Form 2 XRPD pattern.

TABLE 6

Vapour Diffusion physical properties analyses results

| Solvent | Anti-solvent | Crystal form |
|---|---|---|
| Methanol | Diisopropyl ether | Form 2 + unknown peaks |
|  | Ethyl acetate | Form 1 |
| Methanol/water 90/10 | Diisopropyl ether | Form 2 + unknown peaks |
|  | Ethyl acetate | Form 1 + Form 2 |
| Ethanol/water 90/10 | Diisopropyl ether | Form 2 + unknown peaks |
|  | Isopropyl acetate | Form 1 |
| 2-propanol/water 90/10 | Diisopropyl ether | Form 2 + unknown peaks |
|  | Isopropyl acetate | Form 1 + unknown peaks |
|  | Heptane | Form 2 |

Scale Ups 1 g of Compound 2 was weighed in a reaction tube. The starting material was suspended in 15 mL of isopropyl acetate. The slurry was stirred for 15 days at 20° C. After this time the product was filtered to obtain a white solid. The solid was analyzed by XRPD before drying to observe the presence of Form 1 and some unknown peaks. The material was dried in a vacuum oven at 40° C. overnight. The dried material was analyzed by XRPD to show the presence of Form 1 material. FIG. 1 shows the XRPD spectrum of dried material. The spectrum is consistent with Form 1 typical pattern.

Figure 2:
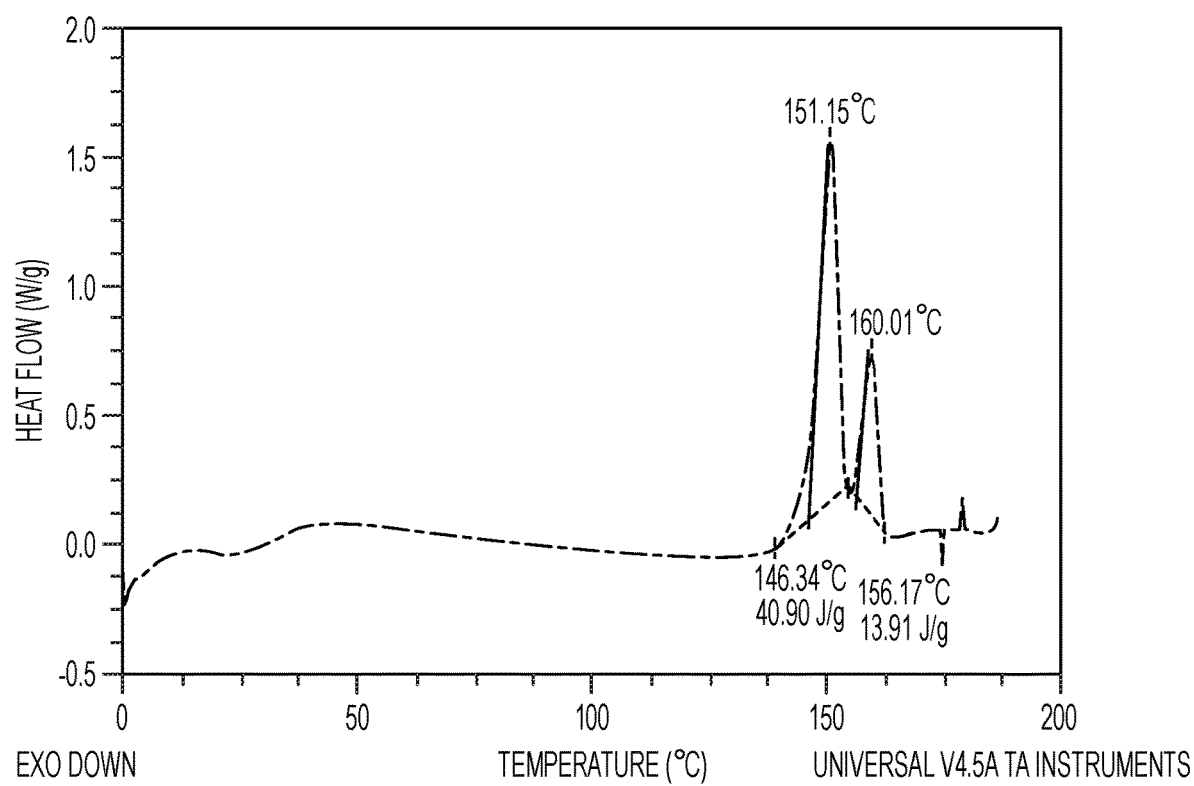
FIG. 2 shows DSC data for Compound 2 Form 1 (with some Compound 2 Form 2 present).

The material obtained was also characterized by DSC, GVS, HPLC, NMR and PLM. The DSC trace showed the presence of a slight quantity of Form 2 material not detected by XRPD. The presence of Form 2 in the DSC sample could be due to amorphous material converted to Form 2 during the DSC heating ramp (FIG. 2).

Figure 3:
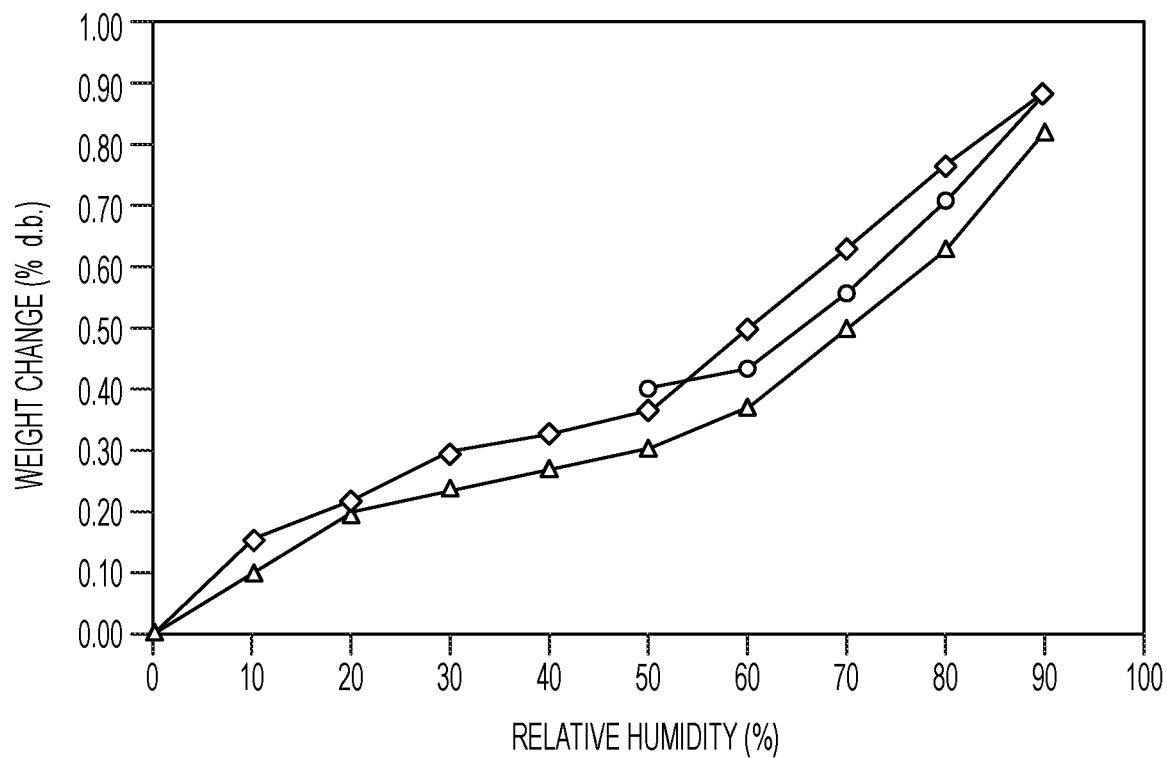
FIG. 3 shows GVS data for Compound 2 Form 1.
Figure 4:
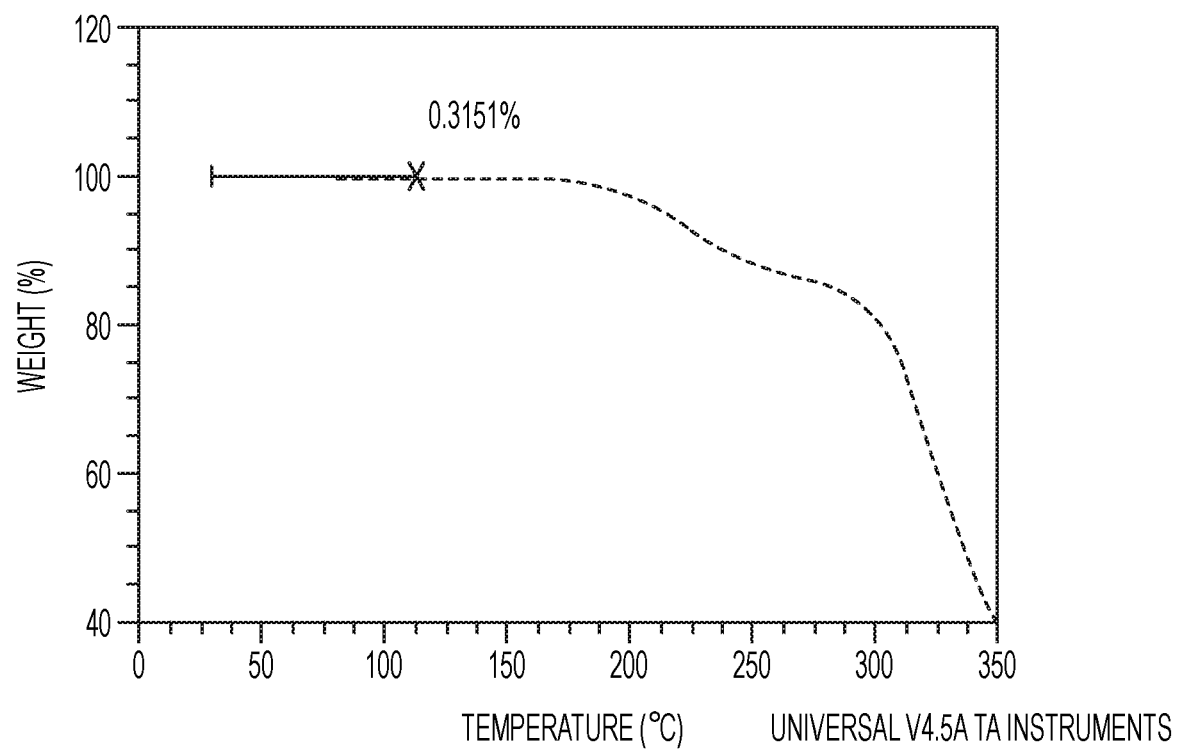
FIG. 4 shows TGA data for Compound 2 Form 1.

The GVS pattern does not highlight increased hygroscopicity of the material (see FIG. 3). The NMR spectrum was consistent with the Compound 2 structure. Succinic acid stoichiometry was assessed to 1:1.

Example 4: Protocol for Human B Cell Stimulation

Human B cells are purified from 150 mL of blood. Briefly, the blood can be diluted 1/2 with PBS and centrifuged through a Ficoll density gradient. The B cells can be isolated from the mononuclear cells by negative selection using the B cell isolation kit II from Milenyi (Auburn, Calif.). 50,000 B cells per well can then be stimulated with 10 ug/mL of goat F(ab')2 anti-human IgM antibodies (Jackson ImmunoResearch Laboratories, West Grove, Pa.) in a 96-well plate. Compounds can be diluted in DMSO and added to the cells. Final concentration of DMSO is 0.5%. Proliferation can be measured after 3 days using Promega CellTiter-Glo (Madison, Wis.).

Example 5: In Vitro BTK Kinase Assay: BTK-POLYGAT-LS ASSAY

The purpose of the BTK in vitro assay is to determine compound potency against BTK through the measurement of IC50. Compound inhibition can be measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction can be done in a black 96 well plate (costar 3694). For a typical assay, a 24 μL aliquot of a ATP/peptide master mix (final concentration; ATP 10 μM, polyGAT 100 nM) in kinase buffer (10 mM Tris-HCl pH 7.5, 10 mM MgCl$_2$, 200 μM Na$_3$PO$_4$, 5 mM DTT, 0.01% Triton X-100, and 0.2 mg/mL casein) can be added to each well. Next, 1 μL of a 4-fold, 40× compound titration in 100% DMSO solvent can be added, followed by addition of 15 μL of BTK enzyme mix in 1× kinase buffer (with a final concentration of 0.25 nM). The assay can be incubated for 30 minutes before being stopped with 28 μL of a 50 mM EDTA solution. Aliquots (5 μL) of the kinase reaction can be transferred to a low volume white 384 well plate (Corning 3674), and 5 μL of a 2× detection buffer (Invitrogen PV3574, with 4 nM Tb-PY20 antibody, Invitrogen PV3552) can be added. The plate can be covered and incubated for 45 minutes at room temperature. Time resolved fluorescence (TRF) on Molecular Devices M5 (332 nm excitation; 488 nm emission; 518 nm fluorescein emission) can be measured. IC$_{50}$ values can be calculated using a four parameter fit with 100% enzyme activity determined from the DMSO control and 0% activity from the EDTA control.

Example 6: Phase 1a Single-Dose Study in Humans

A first-in-human Phase 1a randomized, double-blind, placebo-controlled, single-dose study, was conducted in 3 stages: In Stage 1, four sequential cohorts of 8 subjects each were randomly assigned to receive progressively higher single oral administrations of Compound 2 at doses of 50, 100, 200, and 300 mg (n=6 per cohort; 3 males and 3 females) or placebo (n=2 per cohort; 1 male and 1 female).

In Stage 2, the effects of food on the pharmacokinetics of Compound 2 were assessed. In this stage, 12 newly enrolled subjects (6 males, 6 females; Cohort 6) were administered Compound 2 on two separate occasions, either in a fasting or fed state, with a period of ≥72 hours between the two doses. The Compound 2 dose level was 200 mg. The 12 subjects were randomized such that 6 subjects (3 males, 3 females) received Compound 2 after an overnight fast, and 6 subjects (3 males, 3 females) received Compound 2 after ingestion of a standardized, high-fat meal. Approximately 4 days later, the subjects were crossed over so that those who received Compound 2 without food in the first period then received the drug with food, while those who received Compound 2 with food in the first period then received the drug without food.

Stage 3 evaluated 12 subjects from Cohort 6 who had already received Compound 2 in Stage 2 of the study. Compound 2 at a dose of 25 mg was administered once in the fasted state on Day 1 and subjects were followed for safety, PK and PD evaluations. On Day 4, subjects then received itraconazole (a potent CYP3A4 inhibitor) that was administered at a dose of 200 mg twice daily on Days 4 through 9 in the fed state (except at the morning dose on Day 7). In the morning of Day 7, subjects received itraconazole at a dose of 200 mg followed shortly by administration of Compound 2 at a dose of 25 mg (with both drugs given in the fasted state). Subjects were then followed for safety, PK and PD evaluations on Days 7, 8, 9, and 10. PK results observed following administration of Compound 2 alone on Day 1 were compared with those observed in these same subjects after administration of Compound 2 with itraconazole on Day 7.

The primary endpoint of safety was assessed by monitoring adverse events (AEs), laboratory abnormalities, and cardiac findings (ECG). Secondary endpoints included evaluation of the PK parameters of area under the plasma concentration-time curve (AUC), maximum plasma concentration (Cmax), time of maximum concentration (Tmax), apparent volume of distribution (Vd/F), terminal elimination half-life (t1/2), terminal elimination rate constant (λz), and apparent clearance (Cl/F) as well as the PD parameter of BTK inhibition in whole blood.

Compound 2 is a succinate salt. Plasma concentrations of the free base (Compound 1) were measured and used for estimation of PK parameters and elaboration of concentration/PD relationships.

BTK inhibition was calculated based on phosphorylated BTK (pBTK) and total BTK (totBTK). All postdose blood samples and one predose sample were lysed in the presence of protease and phosphatase inhibitors (PPi); a second predose sample was lysed without PPi to estimate maximum reduction in pBTK attainable. The ratio of predose pBTK/totBTK without PPi was subtracted from each pBTK/totBTK with PPi, and % pBTK vs predose was calculated:

$$\% \ pBTK \text{ vs predose} = \frac{pBTK/totBTK \text{ postdose}}{pBTK/totBTK \text{ predose}} \times 100$$

% BTK inhibition was then calculated:

% BTK inhibition=100−(% pBTK vs predose)

Results

Demographics

The median age for the 24 subjects who received Compound 2 was 55 years (range: 22-64); among the 8 subjects who received placebo, the median age was 42.5 years (range: 29-65). A majority of the subjects who received Compound 2 were Caucasian (95.8%); only 1 subject in cohort 1 (4.2%) was an American Indian/Alaska native.

Safety Findings

Treatment-emergent AEs (TEAEs) were reported for 8 (33%) subjects who received Compound 2 and for 3 (38%) subjects who received placebo. Six (25%) subjects who received Compound 2 had treatment-related TEAEs compared with 3 (38%) subjects who received placebo.

For subjects who received Compound 2, treatment-related TEAEs included headache, nausea, and supraventricular tachycardia; additional reported TEAEs included constipation, bronchitis, fatigue, and orthostatic hypotension. No obvious pattern of dose-dependent toxicity was observed. In the placebo group, all TEAEs were considered treatment-related and included headache, nausea, and diarrhea.

AEs were all reported as Grade 1 except for 1 subject (who received 300 mg Compound 2) who experienced Grade 2 headache and fatigue. No Grade 3 or higher AEs were reported. No SAEs were reported. None of the reported AEs, laboratory abnormalities, or ECG or telemetry findings were considered clinically meaningful.

PK/PD Results

Figure 12:
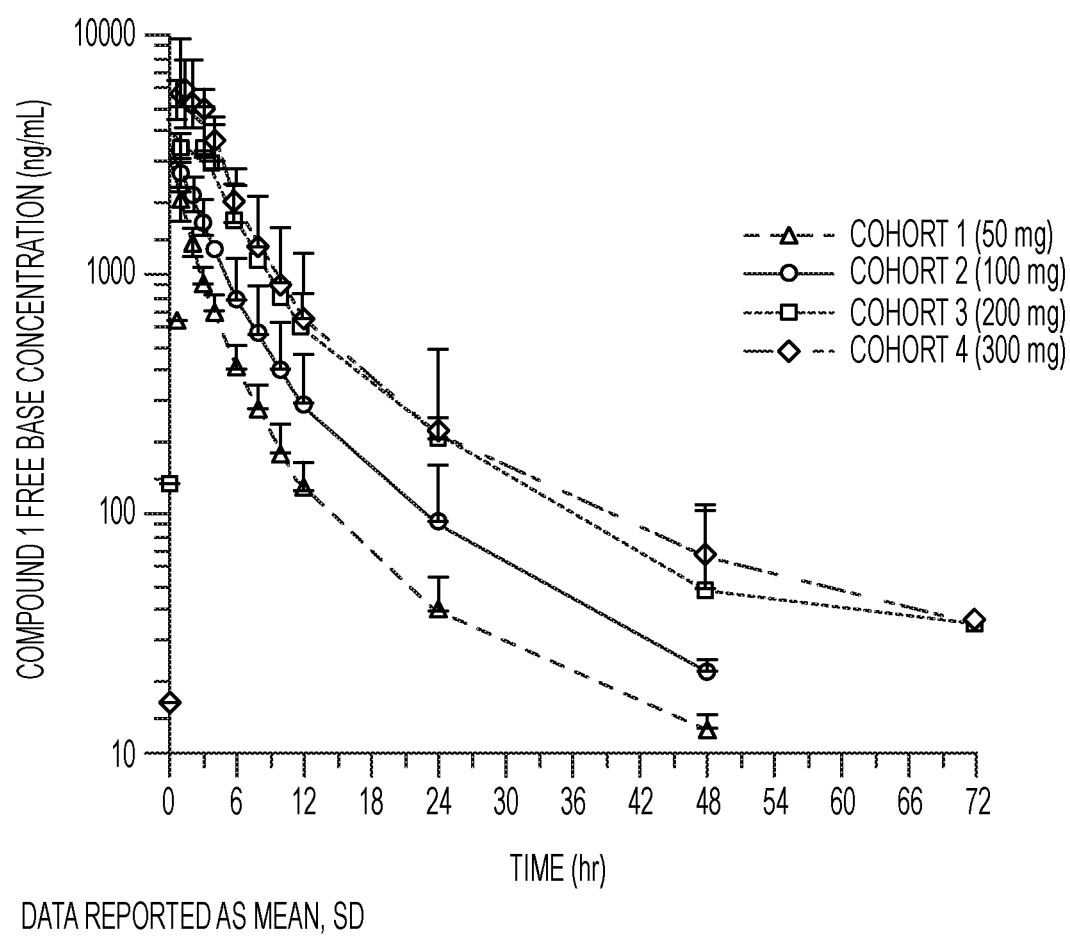
FIG. 12 shows mean Compound 1 plasma concentration vs. time in a single-dose human study administering Compound 2.
Figure 13:
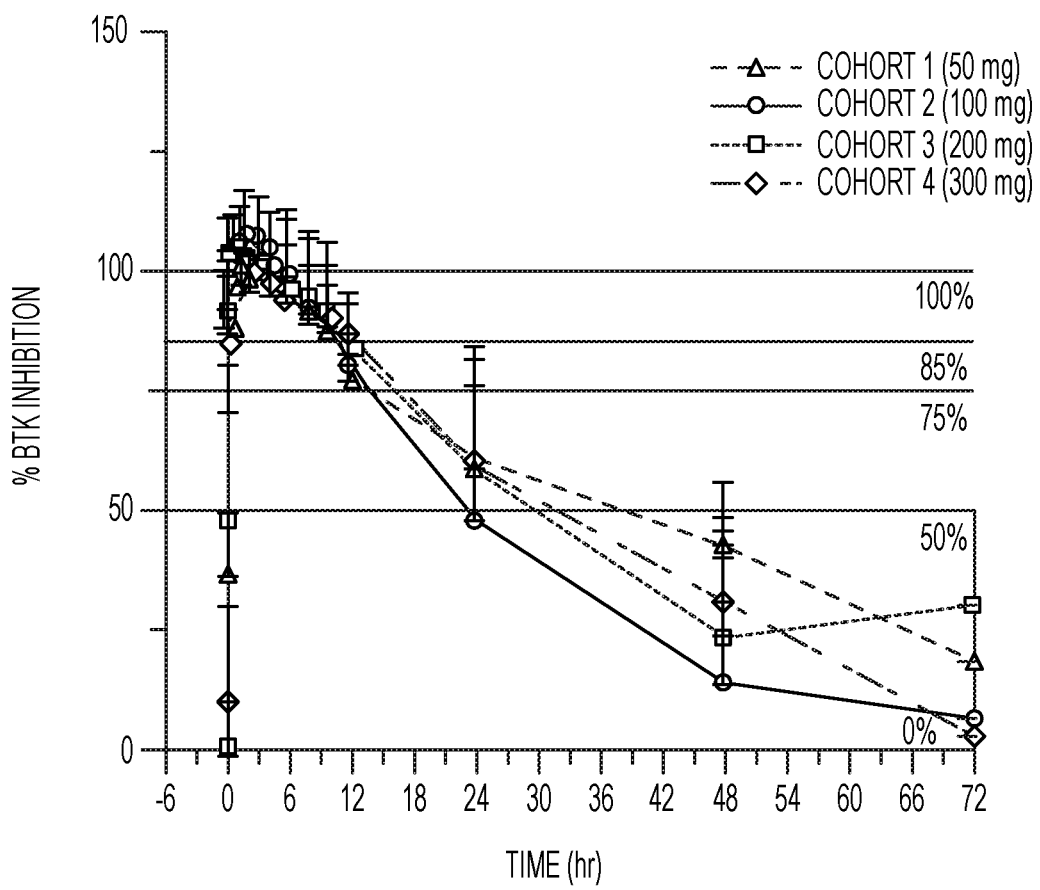
FIG. 13 shows percent BTK inhibition vs. time in a single-dose human study administering Compound 2.

The compound was rapidly absorbed, with a median Tmax=1 hour (range: 0.5-3.0). Mean t1/2 values across all dose cohorts ranged from 7.43 to 17 hours. Compound 1 concentrations declined in a multiphasic manner as shown in FIG. 12. Mean PK parameters for each cohort are shown in Table 7. Total exposure (AUC and Cmax) increased approximately proportionally with dose. The compound demonstrated rapid, profound (~100%), and prolonged inhibition of pBTK at all dose levels, as shown in FIG. 13.

TABLE 7

Summary of Compound 1 Pharmacokinetic Parameters[a]

|  | Cohort 1 (50 mg) | Cohort 2 (100 mg) | Cohort 3 (200 mg) | Cohort 4 (300 mg) |
|---|---|---|---|---|
| N | 6 | 6 | 6 | 6 |
| $C_{max}$ (ng/mL) | 1913 (309) | 3404 (872) | 5956 (3388) | 6795 (1572) |
| $AUC_{0-24}$ (ng*hr/mL) | 7826 (1347) | 14505 (4585) | 29904 (20246) | 35406 (6225) |
| $T_{max}$ (hr) | 1.17 (0.258) | 1.25 (0.88) | 1.00 (0) | 1.50 (0.837) |
| CL/F (mL/hr) | 6139 (1250) | 7162 (2900) | 7886 (3724) | 7615 (1595) |
| Vd/F (mL) | 69580 (9419) | 72948 (21039) | 117823 (59878) | 177190 (68755) |
| $t_{1/2}$ (hr) | 8.14 (2.0) | 7.43 (1.7) | 10.49 (2.6) | 17.00 (8.4) |

[a]Data reported as mean (SD)

$AUC_{0-24}$, area under the concentration-time curve from time 0 to 24 hours; CL/F, apparent clearance; $C_{max}$, maximum plasma concentration; $t_{1/2}$, terminal elimination half-life; Vd/F, apparent volume of distribution.

Figure 14:
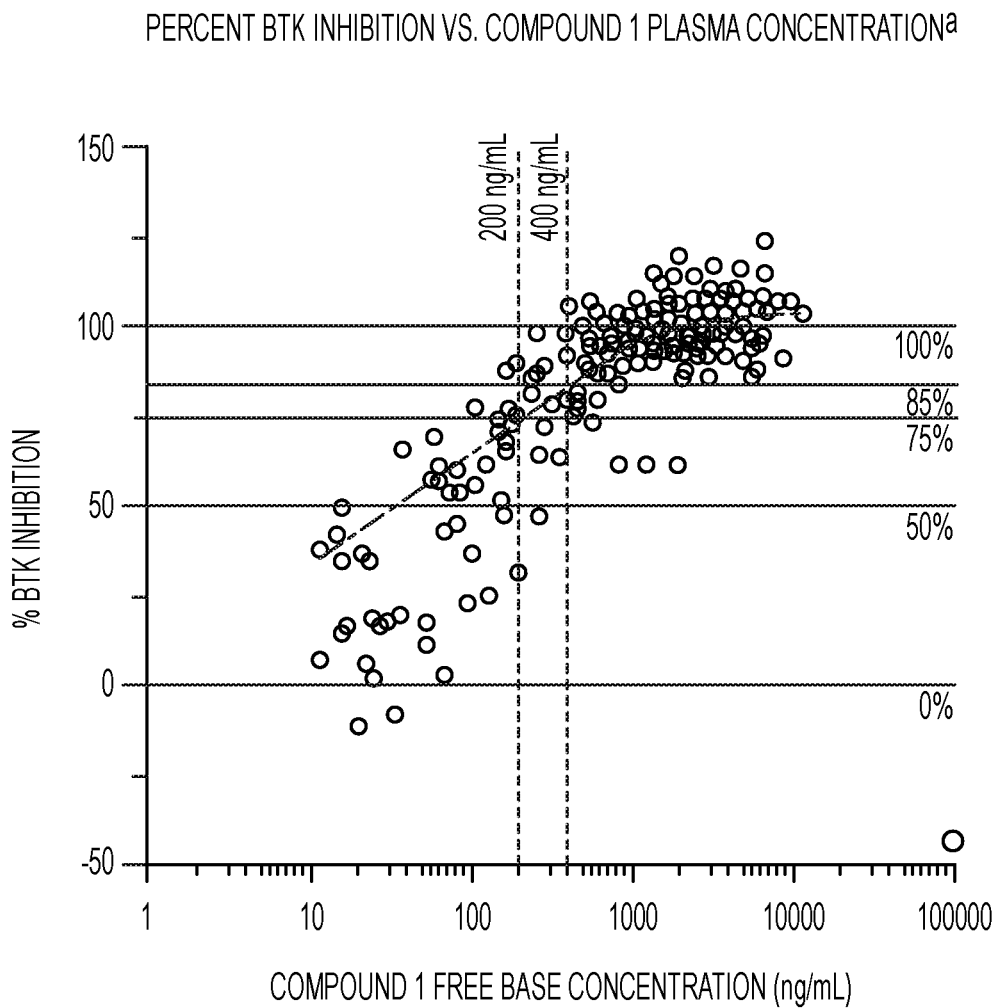
FIG. 14 shows percent BTK inhibition vs. Compound 1 plasma concentration in a single-dose human study administering Compound 2.

The extent of pBTK inhibition at different plasma concentrations is shown in FIG. 14. Although a specific target level of pBTK inhibition for clinical efficacy has not yet been reported, it is expected that approximately 85% inhibition is generally sufficient for clinical activity (Byrd J C, et al. *N Engl J Med.* 2016; 374:323-32).

Food Effect

The effects of food on the pharmacokinetics of Compound 2 were assessed after oral administration of 200 mg Compound 2 to 12 subjects in the fed and fasted states. The absorption rate of Compound 2 in fed state was decreased, with Tmax delayed by 2 hours and $C_{max}$ decreased by about 30%; however, there was no impact on the extent of absorption (AUC) and elimination (T½) of Compound 2. Similarly, apparent total body clearance and volume of distribution were comparable in both food conditions. Overall, the results indicate that Compound 2 may be given with or without food.

Drug-Drug Interaction (Effect of CYP3A4 Inhibition)

The effect of the strong CYP3A4 inhibitor, itraconazole, on the pharmacokinetics of an oral dose of 25 mg Compound 2 was evaluated in 12 subjects (Table 7a). When itraconazole was coadministered with Compound 2, an increase of Compound 1 plasma exposure ($C_{max}$ and AUCs) of about 2-fold and 6.3 to 7.0-fold, respectively was observed. These results indicate that Compound 1 is a sensitive substrate for CYP3A4 (i.e., shows a ≥5-fold increase in exposure in the presence of CYP enzyme inhibition). Based on these data, there may be constraints on enrollment of subjects requiring coadministration of drugs that are moderate or strong CYP3A4 inhibitors or inducers and there may be restrictions on use of such drugs during protocol therapy.

TABLE 7a

| PK parameter | Compound 2 25 mg fasted N = 12 | Compound 2 25 mg fasted + itraconazole N = 12 | Compound 2 25 mg fasted + itraconazole vs. Compound 2 25 mg fasted | |
|---|---|---|---|---|
| | | | PE | 90% CI |
| $C_{max}$ (ng/mL) | 873 (24.9) | 1684 (17.4) | 196.54 | 173.39, 222.79 |
| $t_{max}$ (hr) | 1.00 (0.50, 2.00) | 1.50 (1.00, 2.00) | 0.75 | 0.50, 1.00 |
| $AUC_{0-t}$ (ng·hr/mL) | 4425 (44.1) | 28026 (21.3) | 671.87 | 575.51, 784.37 |
| $AUC_{inf}$ (ng·hr/mL) | 4618 (43.6) | 32182 (23.6)[a] | 742.55 | 627.80, 878.26 |
| $T_{1/2}$ (hr) | 6.90 (30.4) | 27.3 (22.7) | | |
| CL/F (L/hr) | 6.34 (41.6) | 0.828 (29.8)[a] | | |
| Vz/F (L) | 57.5 (22.4) | 30.4 (26.1)[a] | | |

Values are arithmetic means (CV %) except for tmax (median (min, max)).
PE and 90%CI: Point estimate and 90% CI of the least-squares geometric means ratio (ANOVA); median of difference and non-parametric 90% CI calculated by method of Hodges-Lehmann for tmax.
[a]N = 11 subjects with available data
Abbreviations: $AUC_{inf}$ = area under the concentration-time curve from time 0 to infinity; $AUC_{0-t}$ = area under the concentration-time curve from time 0 to the time of last measurable concentration; CL/F=; Cmax = maximum concentration; N = number of subjects in the cohort; PK = pharmacokinetics; PD = pharmacodynamics; $T_{1/2}$ = terminal plasma elimination half-life; Vz/F = Apparent volume of distribution during terminal phase after oral/extravascular administration.

Pharmacokinetic/Pharmacodynamic Relationship

Figure 15:
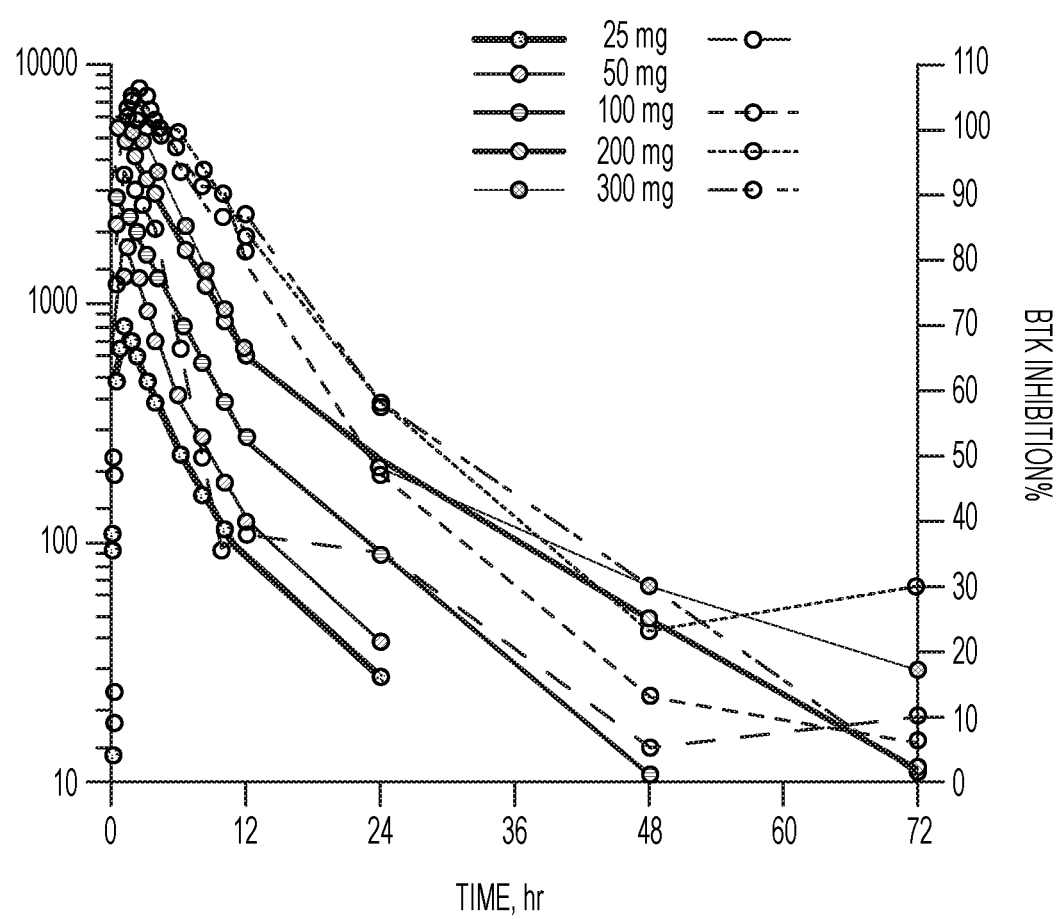
FIG. 15 shows Compound 2 concentrations (ng/mL) and percent BTK inhibition vs. time. Compound 2 50 mg not displayed for % BTK inhibition.
Figure 16:
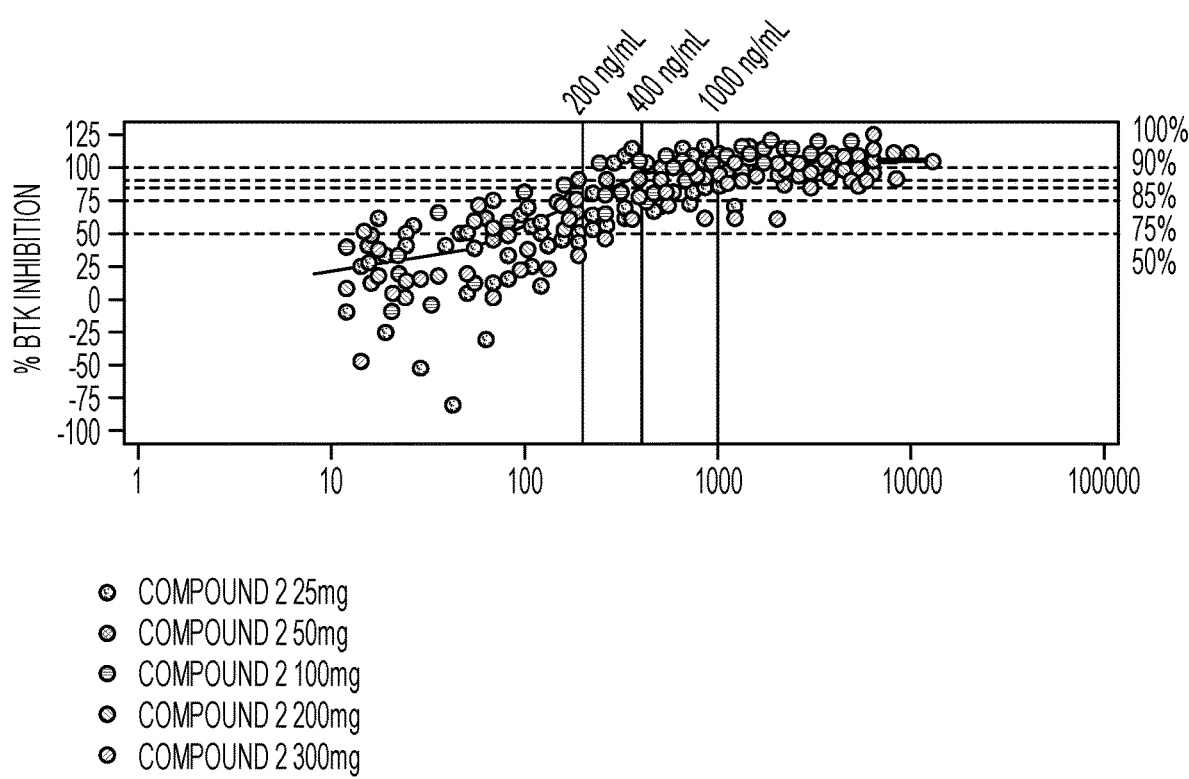
FIG. 16 shows the correlation between % BTK inhibition and Compound 1 plasma concentrations (x axis, ng/mL) following administration of Compound 2, from Stage 1+Stage 3 (Compound 2 25 mg alone) dosing described below.

Correlation between PK and PD measurements (Compound 1 plasma concentration vs. % BTK inhibition) for Stage 1 (100, 200, and 300 mg) and Stage 3 (25 mg alone) is presented per time point (FIG. 15) and overall (scatter plot with LOESS regression curve and 95% confidence interval; FIG. 16). A clear correlation was observed between PK and PD. When Compound 1 plasma concentrations were lower or close to 100 ng/mL the % BTK inhibition was no greater than 75%. Inhibition of pBTK of 85% and higher was observed with Compound 1 plasma concentrations ≥200 ng/mL. As concentrations increased inhibition increased and was less variable. For most of the subjects, plasma concentrations above 1000 ng/mL produced inhibition >85% and largely around 100%.

Conclusions

Compound 2 showed favorable safety and PK/PD profiles in healthy subjects. Mean exposure at the lowest dose of 50 mg exceeded exposures reported for both ibrutinib (Binnerts M E, et al. Mol Cancer Ther. 2015; 14 (12 Suppl 2); IMBRUVICA® (ibrutinib) capsules, for oral use [prescribing information]). Sunnyvale, Calif.: Pharmacyclics LLC.; 2016; Center for Drug Evaluation and Research. 205552 Clinical pharmacology review (Imbruvica™). Jul. 30, 2013) and acalabrutinib (Byrd J C, et al. N Engl J Med. 2016; 374:323-32) when administered at their respective recommended dose levels (Table 8).

TABLE 8

Mean Pharmacokinetic Parameters for BTK Inhibitors (after dosing with Compound 2)

| | $C_{max}$ (ng/mL) | $AUC_{0-24}$ (ng*hr/mL) | $t_{1/2}$ (hr) |
|---|---|---|---|
| Compound 1 50 mg (single dose) | 1913 | 7826 | 8.14 |
| Acalabrutinib 100 mg BID (steady state)[3] | 827 | 1850 | 1.13 |
| Ibrutinib 560 mg (single dose)[9] | 141 | 682 | —[a] |

[a]$t_{1/2}$ evaluable for 2 of 9 patients only and was 6.1 hr
$AUC_{0-24}$, area under the plasma concentration-time curve from time 0 to 24 hours; BID, twice daily; BTK, Bruton's tyrosine kinase; $C_{max}$, maximum plasma concentration, $t_{1/2}$, terminal elimination half-life.

These results indicate that Compound 2 has improved PK properties, including bioavailability and half-life, over these covalent inhibitors. The pharmaceutical properties of Compound 2 are expected to allow maintenance of sufficient serum concentrations to provide sustained inhibition of BTK, resulting in potential clinical benefit.

The safety profile, extent of Compound 2 exposure, and duration of pBTK inhibition are encouraging. These data support twice-daily dosing to assess safety and activity in a planned phase 1b/2 study in patients with advanced B-cell malignancies with and without BTK Cys481 mutations.

Example 7: Pharmacokinetics of Compound 2

A series of single-dose PK studies were conducted in rat, dog, and monkey to investigate the plasma PK of Compound 2 following single oral and single intravenous (IV) administration of Compound 2. The results are summarized in Table 9 and described in detail below.

TABLE 9

| Species | Route | Dose | Formulation | $T_{max}$ (h) | $T_{1/2}$ (h) | $C_0$ (ng/ml) | $C_{max}$ (ng/ml) | $AUC_{inf}$ (ng·h/ml) | % F |
|---|---|---|---|---|---|---|---|---|---|
| Rat | IV | 1 | SPEW | NA | 4.0 | 4371 | NA | 16105 | |
| | PO | 5 | 0.1% CMC/ 0.2% Tween | 2.6 | NA | NA | 1775 | 14590 | 18 |
| Dog | IV | 1 | 70% PEG400/ H$_2$O | NA | 0.8 | 1925 | NA | 1081 | |

TABLE 9-continued

| Species | Route | Dose | Formulation | $T_{max}$ (h) | $T_{1/2}$ (h) | $C_0$ (ng/ml) | $C_{max}$ (ng/ml) | $AUC_{inf}$ (ng · h/ml) | % F |
|---|---|---|---|---|---|---|---|---|---|
| | PO | | 0.1% CMC/ 0.2% Tween | 0.8 | NA | NA | 2973 | 3516 | 65 |
| Monkey | IV | 1 | 70% PEG400/ H₂O | NA | 1.9 | 1605 | NA | 1921 | |
| | PO | 5 | 0.1% CMC/ 0.2% Tween | 1.5 | NA | NA | 1401 | 3224 | 33 |

Note:
All animals received Compound 2; PK results represent the free base (Compound 1). Abbreviations:
% F = oral bioavailability;
C0 = initial concentration;
Cmax = maximum plasma concentration;
CMC = carboxymethylcellulose;
IV = intravenous;
NA = not applicable;
PEG400 = polyethylene glycol 400;
PK = pharmacokinetic;
PO = oral;
SPEW = Solutol ®:PEG400:ethanol:water (1:1:1:7);
T½ = terminal half-life;
Tmax = time to maximum concentration The PK profile of Compound 2 was evaluated in male Sprague Dawley rats (n=3) following single IV administration of Compound 2 at 1 mg/kg and single oral administration at 5 mg/kg. Following each administration serial blood samples were collected at 0 (predose), 0.08, 0.25, 0.5, 0.75, 2, 5, 10, and 24 hours postdose. PK parameters are reported in Table 9.

A study was conducted to assess the PK of Compound 2 formulated as a suspension or as a solid in capsule. Male beagle dogs (n=3) received a single oral gavage administration at 35 and 200 mg/kg (DRN105-0001) as a suspension in 0.5% w/v K15 M and 0.2% w/v sodium dodecyl sulfate (SDS) in sterile water for injections or as powder in capsule. Three different dogs were used for each dose level. The dogs used for the 35 mg/kg oral dose then received a single IV bolus administration of 5 mg/kg Compound 2 formulated in 10% w/v hydroxypropyl cyclodextrin in citrate buffer pH 4.5. Inter-animal variability in Compound 2 free base plasma systemic exposure was observed after IV and oral administration irrespective of formulation. See Table 9.

The PK of Compound 2 was studied in the male cynomolgus monkey (n=3) following single IV administration of Compound 2 at 1 mg/kg and single oral administration at 5 mg/kg (DRN105-0042). Following each administration, serial blood samples were collected at 0.08, 0.25, 0.5, 1, 2, 4, 7, 16, and 24 hours postdose. Data were analyzed using noncompartmental PK analysis (WinNonlin) and PK parameters are reported in Table 9.

Example 8: Compound 1 Inhibits C481S Mutated Bruton Tyrosine Kinase Overcoming Resistance to Ibrutinib In order to address the issue of acquired resistance to ibrutinib, this Example characterizes the Bruton tyrosine kinase (BTK) inhibitor Compound 1 in preclinical models of chronic lymphocytic leukemia (CLL).

Methods: Primary CLL B cells were isolated from the whole blood of consented patients by FICOLL density centrifugation and rosette-sep negative selection. Annexin V and propidium iodide flow cytometry was used to measure patient CLL cell viability and 7AAD was used to measure viability in stromal co-culture. $CD_{40}$ and $CD_{86}$ expression was evaluated via flow cytometry subsequent to sustained 3.2 µM CpG stimulation. BCR signaling in primary CLL cells was investigated by immunoblot succeeding 1 hour treatment and following 1 hour or 24 hours of incubation with Compound 1 in XLA cell lines. MTS values were read after 24 hours of drug incubation. ITK inhibition was investigated via immunoblot after stimulation with anti-CD3 and anti-CD28 and incubation with Compound 1 for 1 hour. Compound 1 was used at a concentration of 1 µM in preclinical studies unless otherwise noted. Measurement of kinase activity in human recombinant WT BTK or C481S BTK was performed in a FRET kinase assay.

Results: Immunoblots of BTK and ERK phosphorylation of XLA cells transfected with WT or C481S BTK demonstrated that Compound 1 inhibition is comparable to that of ibrutinib in WT BTK and greater than that of ibrutinib in C481S BTK. Using a recombinant kinase assay, it was found the IC50 of Compound 1 against WT BTK to be 4.6 nM and C481S BTK to be 1.1 nM, suggesting that Compound 1 is more effective in the mutated BTK variant. Additionally, Compound 1 was found to be six times more potent than ibrutinib and greater than 640 times more potent than acalabrutinib against C481S BTK.

Compound 1 demonstrates dose-dependent inhibition of BTK in primary patient CLL cells comparable to ibrutinib via immunoblot for BTK phosphorylation. The viability of primary patient cells treated with 0.1 µM, 1.0 µM, and 10.0 µM Compound 1 for 48 hours was measured to be 96.7%, 96.1%, and 88.1%, respectively, that of the untreated condition. At 48 hours Compound 1 decreased viability of primary CLL cells in the presence of HS5 stromal protection by 5.5%. Compound 1 was found to decrease CpG induced CD40 and CD86 expression by 8.7% and 15.7%, respectively. An immunoblot of anti-CD3 and anti-CD28 stimulated Jurkat cells revealed that Compound 1 decreased the phosphorylation of ERK implying inhibition of ITK.

Conclusion: Unlike ibrutinib, Compound 1 decreases BTK phosphorylation in C481S BTK. Compound 1 decreases B cell activation markers, viability, and stromal cell protection in primary patient CLL cells and was shown to inhibit ITK.

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A solid form Compound 2 comprising Compound 1 and succinic acid:

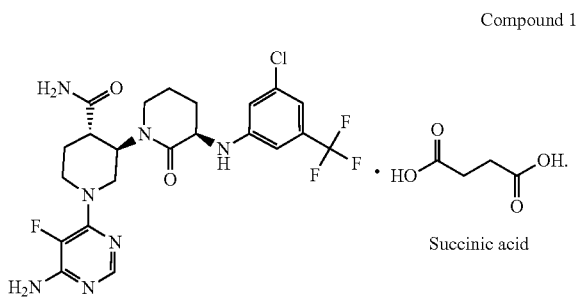 [SMILES: NC(=O)[C@H]1CCN(c2ncnc(N)c2F)C[C@@H]1N1CCC[C@@H](Nc2cc(Cl)cc(C(F)(F)F)c2)C1=O ; O=C(O)CCC(=O)O]

2. The solid form of claim 1, wherein said solid form is a crystalline solid.

3. The solid form of claim 2, wherein said solid form is Form 1.

4. The solid form of claim 3, having one or more peaks in its X-ray powder diffraction pattern at about 5.33, about 7.59, about 9.75, about 13.69, about 17.91, about 18.14, about 20.12, or about 24.73 degrees 2-theta.

5. The solid form of claim 4, having a XRPD substantially similar to that depicted in FIG. 1.

6. The solid form of claim 2, wherein said compound is Form 2.

7. The solid form of claim 6, having one or more peaks in its X-ray powder diffraction pattern at about 6.76, about 8.77, about 9.06, about 12.00, about 13.53, about 18.13, or about 20.07 degrees 2-theta.

8. The solid form of claim 7, having a XRPD substantially similar to that depicted in FIG. 5.

9. The solid form of claim 1, wherein said solid form is an amorphous solid form.

10. A composition comprising the solid form of claim 1 and a pharmaceutically acceptable carrier or excipient.

11. A method of treating a disorder responsive to inhibition of Bruton's tyrosine kinase comprising administering to a subject an effective amount of the solid form of claim 1 or a composition thereof, wherein the disorder is selected from chronic lymphocytic leukemia, acute lymphocytic leukemia, diffuse Large B-cell lymphoma, rheumatoid arthritis, non-Hodgkin lymphoma, and Waldönstrom's macroglobulinemia.

12. A method of treating a disorder selected from chronic lymphocytic leukemia, acute lymphocytic leukemia, diffuse Large B-cell lymphoma, rheumatoid arthritis, non-Hodgkin lymphoma, and Waldönstrom's macroglobulinemia comprising administering to a subject an effective amount of the solid form of claim 1 or a composition thereof.

13. The method of claim 12, wherein the effective amount of a solid form or a composition thereof is about 25 mg to about 300 mg.

14. The method of claim 13, wherein the solid form or composition thereof, is administered once, twice, or more than twice daily.

15. A unit dosage form of the solid form of claim 1 and a pharmaceutically acceptable carrier or excipient.

16. The unit dosage form of claim 15, comprising an amount of Compound 2 that is about 25 mg to about 300 mg.

17. An oral formulation comprising the solid form of claim 1 and a pharmaceutically acceptable carrier or excipient.

18. A method of treating a subject having a disorder responsive to inhibition of BTK, in which the subject has been treated with a first BTK inhibitor and has acquired a functional BTK Cys481 mutation that impairs the activity of the first BTK inhibitor, comprising administering to the subject an effective amount of Compound 1, a solid form of claim 1, or a composition thereof, wherein the disorder is selected from chronic lymphocytic leukemia, acute lymphocytic leukemia, diffuse Large B-cell lymphoma, rheumatoid arthritis, non-Hodgkin lymphoma, and Waldönstrom's macroglobulinemia.

19. The method of claim 18, wherein the mutation is C481S, C481F, C481G, or C481T.

* * * * *